United States Patent
Clark et al.

(10) Patent No.: US 9,856,290 B2
(45) Date of Patent: Jan. 2, 2018

(54) GLYCOPEPTIDE COMPOSITIONS AND USES THEREOF

(71) Applicant: SUSSEX RESEARCH LABORATORIES INC., Ottawa (CA)

(72) Inventors: Kenneth Brady Clark, Ottawa (CA); Remmick So, Nepean (CA); Vanja Vukic, Ottawa (CA)

(73) Assignee: Sussex Research Laboratories Inc., Ottawa (CA)

( * ) Notice: Subject to any disclaimer, the term of this patent is extended or adjusted under 35 U.S.C. 154(b) by 0 days.

(21) Appl. No.: 15/103,452

(22) PCT Filed: Dec. 9, 2014

(86) PCT No.: PCT/CA2014/051190
§ 371 (c)(1),
(2) Date: Jun. 10, 2016

(87) PCT Pub. No.: WO2015/085421
PCT Pub. Date: Jun. 18, 2015

(65) Prior Publication Data
US 2016/0304561 A1 Oct. 20, 2016

Related U.S. Application Data

(60) Provisional application No. 61/914,309, filed on Dec. 10, 2013.

(51) Int. Cl.
| | |
|---|---|
| *C07K 7/06* | (2006.01) |
| *A61Q 19/00* | (2006.01) |
| *A61K 38/08* | (2006.01) |
| *A61K 8/64* | (2006.01) |
| *A61Q 19/08* | (2006.01) |
| *A61K 45/06* | (2006.01) |
| *A61K 38/00* | (2006.01) |

(52) U.S. Cl.
CPC .................. *C07K 7/06* (2013.01); *A61K 8/64* (2013.01); *A61K 38/08* (2013.01); *A61K 45/06* (2013.01); *A61Q 19/007* (2013.01); *A61Q 19/08* (2013.01); *A61K 38/00* (2013.01)

(58) Field of Classification Search
CPC .......... A61K 8/64; A61K 38/08; A61K 45/06; A61K 38/00; C07K 7/06; A61Q 19/08; A61Q 19/007
See application file for complete search history.

(56) References Cited

U.S. PATENT DOCUMENTS

| | | |
|---|---|---|
| 1,985,424 A | 12/1934 | Piggott |
| 2,438,091 A | 3/1948 | Lynch |
| 2,528,378 A | 10/1950 | Mannheimer |
| 2,658,072 A | 11/1953 | Kosmin |
| 2,703,798 A | 3/1955 | Schwartz |
| 2,798,053 A | 7/1957 | Brown |
| 2,831,854 A | 4/1958 | Tucker et al. |
| 2,965,576 A | 12/1960 | Wilson |
| 3,155,591 A | 11/1964 | Hilfer |
| 3,755,560 A | 8/1973 | Dickert et al. |
| 3,929,678 A | 12/1975 | Laughlin et al. |
| 3,959,461 A | 5/1976 | Bailey et al. |
| 3,963,699 A | 6/1976 | Rizzi et al. |
| 4,005,195 A | 1/1977 | Jandacek |
| 4,005,196 A | 1/1977 | Jandacek et al. |
| 4,387,090 A | 6/1983 | Bolich, Jr. |
| 4,421,769 A | 12/1983 | Dixon et al. |
| 4,509,949 A | 4/1985 | Huang et al. |
| 4,517,360 A | 5/1985 | Volpenhein |
| 4,518,772 A | 5/1985 | Volpenhein |
| 4,557,853 A | 12/1985 | Collins et al. |
| 4,599,379 A | 7/1986 | Flesher et al. |
| 4,628,078 A | 12/1986 | Glover et al. |
| 4,677,120 A | 6/1987 | Parish et al. |

(Continued)

FOREIGN PATENT DOCUMENTS

| | | |
|---|---|---|
| EP | 228868 | 7/1987 |
| EP | 330369 | 8/1989 |

(Continued)

OTHER PUBLICATIONS

US 5,305,514, 04/1994, Letton et al. (withdrawn)
Goodwin et al, Peptides as Therapeutics with Enhanced Bioactivity, Current Medicinal Chemistry, 2012, 19, pp. 4451-4461.*
Powell et al, Peptide Stability in Drug Development. II. Effect of Single Amino Acid Substitution and Glycosylation on Peptide Reactivity in Human Serum, Pharmaceutical Research, 1993, 10, pp. 1268-1273.*
Office Action dated Aug. 8, 2016 on corresponding Canadian Patent Application No. 2,933,416.
Katayama, K. et al., "A pentapeptide from Type I procollagen promotes extracellular matrix production," J. Biological Chemistry, 1993, vol. 268, No. 14, pp. 9941-9944.

(Continued)

*Primary Examiner* — Julie Ha
*Assistant Examiner* — Li Ni Komatsu
(74) *Attorney, Agent, or Firm* — Borden Ladner Gervais LLP; David A. Nauman

(57) ABSTRACT

The present disclosure provides glycosylated oligopeptides having the sequence Palmitoyl-X1-Lys-X2-X3-Lys-X4-OH, where: X1 is: absent, Ser having a glycosylated side chain, or Asn having a glycosylated side chain; X2 is: Thr, Thr having a glycosylated side chain, Asn having a glycosylated side chain, or Ser having a glycosylated side chain; X3 is: Thr, or Thr having a glycosylated side chain; X4 is: Ser, or Ser having a glycosylated side chain. At least one of X1, X2, X3 and X4 is an amino acid having a glycosylated side chain. Each glycosylated side chain is, independently, glycosylated with a carbohydrate selected from the group consisting of: glucose, N-acetyl-glucosamine, galactose, N-acetyl-galactosamine, mannose, maltose, lactose, rhamnose, cellobiose, xylose, and fucose. Each hydroxyl group on the carbohydrate is, independently, OH or acetylated.

25 Claims, 24 Drawing Sheets

(56) References Cited

U.S. PATENT DOCUMENTS

| | | |
|---|---|---|
| 4,797,300 A | 1/1989 | Jandacek et al. |
| 4,800,197 A | 1/1989 | Kowcz et al. |
| 4,835,148 A | 5/1989 | Barford et al. |
| 4,835,206 A | 5/1989 | Farrar et al. |
| 4,847,071 A | 7/1989 | Bissett et al. |
| 4,849,484 A | 7/1989 | Heard |
| 4,885,311 A | 12/1989 | Parish et al. |
| 4,937,370 A | 6/1990 | Sabatelli |
| 4,960,764 A | 10/1990 | Figueroa, Jr. et al. |
| 4,976,953 A | 12/1990 | Orr et al. |
| 4,999,186 A | 3/1991 | Sabatelli et al. |
| 5,011,681 A | 4/1991 | Ciotti et al. |
| 5,049,584 A | 9/1991 | Purcell et al. |
| 5,073,371 A | 12/1991 | Turner et al. |
| 5,073,372 A | 12/1991 | Turner et al. |
| 5,087,445 A | 2/1992 | Haffey et al. |
| 5,100,660 A | 3/1992 | Hawe et al. |
| 5,120,532 A | 6/1992 | Wells et al. |
| 5,124,356 A | 6/1992 | Purcell et al. |
| 5,151,209 A | 9/1992 | McCall et al. |
| 5,151,210 A | 9/1992 | Steuri et al. |
| 5,306,515 A | 4/1994 | Letton et al. |
| 5,306,516 A | 4/1994 | Letton et al. |
| 5,487,884 A | 1/1996 | Bissett et al. |
| 5,607,980 A | 3/1997 | McAtee et al. |
| 5,652,228 A | 7/1997 | Bissett |
| 5,681,852 A | 10/1997 | Bissett |
| 5,686,082 A | 11/1997 | N'Guyen |
| 5,686,367 A | 11/1997 | Hayashi |
| 5,821,250 A | 10/1998 | Wu et al. |
| 5,972,957 A | 10/1999 | Wu et al. |
| 5,981,547 A | 11/1999 | Wu et al. |
| 5,997,887 A | 12/1999 | Ha et al. |
| 6,492,326 B1 | 12/2002 | Robinson et al. |
| 6,620,419 B1 | 9/2003 | Lintner |

FOREIGN PATENT DOCUMENTS

| | | |
|---|---|---|
| GB | 809060 | 2/1959 |
| GB | 2274585 | 8/1994 |
| WO | 1995/023780 | 9/1995 |
| WO | 1991/16035 | 10/1995 |
| WO | 1995/034280 | 12/1995 |
| WO | 1996/33689 | 10/1996 |
| WO | 1997/21423 | 6/1997 |
| WO | 1997/039733 A1 | 10/1997 |

OTHER PUBLICATIONS

Mas-Chamberline, C. et al., "Relevance of Antiwrinkle Treatment of a peptide: 4 months clinical double blind study vs excipient," Ann. Dermatol. Venereol., 2002, vol. 129, pp. 1S371-1S602.

International Preliminary Report on Patentability for International Application No. PCT/CA2014/051190 dated Jun. 23, 2016.

International Search Report and Written Opinion dated Feb. 23, 2015 for International Application No. PCT/CA2014/051190.

European Patent Application No. 14869829.3, Extended European Search Report dated Oct. 28, 2016.

Moradi et al., "Glycosylation, an Effective Synthetic Strategy to Improve to Bioavailability of Therapeutic Peptides", Chemical Science, Jan. 2016, vol. 7 (4), pp. 2492-2500.

Sederma, "MATRIXYL™: The Messenger Peptide for Dermal Matrix Repair: An Alternative to Retinol and Vitamin C", Mar. 27, 2003, 3 Pages.

European Patent Application No. 14869829.3, Intention to Grant dated Jun. 30, 2017. 7 pages.

\* cited by examiner

```
                          SEQUENCE LISTING

<160> NUMBER OF SEQ ID NOS: 48

<210> SEQ ID NO 1
    <211> LENGTH: 5
    <212> TYPE: PRT
    <213> ORGANISM: Homo sapiens

<400> SEQUENCE: 1

Lys Thr Thr Lys Ser
    1               5

<210> SEQ ID NO 2
    <211> LENGTH: 5
    <212> TYPE: PRT
    <213> ORGANISM: Homo sapiens
    <220> FEATURE:
    <221> NAME/KEY: MOD_RES
    <222> LOCATION: (1)..(1)
    <223> OTHER INFORMATION: having N-terminal palmitoyl

<400> SEQUENCE: 2

Lys Thr Thr Lys Ser
    1               5

<210> SEQ ID NO 3
    <211> LENGTH: 6
    <212> TYPE: PRT
    <213> ORGANISM: Homo sapiens
    <220> FEATURE:
    <221> NAME/KEY: MISC_FEATURE
    <222> LOCATION: (1)..(1)
    <223> OTHER INFORMATION: the amino acid is present or absent; if present
          the amino acid is a serine, or an asparagine
    <220> FEATURE:
    <221> NAME/KEY: MOD_RES
    <222> LOCATION: (1)..(1)
    <223> OTHER INFORMATION: if the amino acid is present, it has a free N-
          terminus, an N-terminal palmitoyl group, or an N-terminal acetyl
          group
    <220> FEATURE:
    <221> NAME/KEY: MOD_RES
    <222> LOCATION: (1)..(6)
    <223> OTHER INFORMATION: at least one of the amino acids has a
          glycosylated side chain; the glycosylated side chains are,
          independently: glucose, N-acetyl-glucosamine, galactose, N-acetyl-
          galactosamine, mannose, maltose, lactose, rhamnose, cellobiose,
          xylose, or fucose
    <220> FEATURE:
    <221> NAME/KEY: MOD_RES
    <222> LOCATION: (2)..(2)
    <223> OTHER INFORMATION: if the amino acid at position 1 is absent, the
          amino acid at position 2 has a free N-terminus, an N-terminal
          palmitoyl group, or an N-terminal acetyl group
    <220> FEATURE:
    <221> NAME/KEY: MISC_FEATURE
    <222> LOCATION: (3)..(3)
```

```
<223> OTHER INFORMATION: the amino acid is threonine, threonine having a
      glycosylated side chain, asparagine having a glycosylated side
      chain, or serine having a glycosylated side chain
<220> FEATURE:
<221> NAME/KEY: MISC_FEATURE
<222> LOCATION: (4)..(4)
<223> OTHER INFORMATION: the amino acid is threonine, or threonine
      having a glycosylated side chain
<220> FEATURE:
<221> NAME/KEY: MISC_FEATURE
<222> LOCATION: (6)..(6)
<223> OTHER INFORMATION: the amino acid is serine, or serine having a
      glycosylated side chain

<400> SEQUENCE: 3

Xaa Lys Xaa Xaa Lys Xaa
1               5

<210> SEQ ID NO 4
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with per-acetylated beta-glucose

<400> SEQUENCE: 4

Lys Thr Thr Lys Ser
1               5

<210> SEQ ID NO 5
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with per-acetylated alpha-mannose

<400> SEQUENCE: 5

Lys Thr Thr Lys Ser
1               5

<210> SEQ ID NO 6
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with per-acetylated beta-maltose

<400> SEQUENCE: 6

Lys Thr Thr Lys Ser
1               5

<210> SEQ ID NO 7
<211> LENGTH: 5
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with per-acetylated beta-galactose

<400> SEQUENCE: 7

Lys Thr Thr Lys Ser
1               5

<210> SEQ ID NO 8
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with per-acetylated beta-glucose

<400> SEQUENCE: 8

Lys Thr Thr Lys Ser
1               5

<210> SEQ ID NO 9
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with peracetylated beta-maltose

<400> SEQUENCE: 9

Lys Thr Thr Lys Ser
1               5

<210> SEQ ID NO 10
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-maltose

<400> SEQUENCE: 10

Lys Thr Thr Lys Ser
1               5

<210> SEQ ID NO 11
<211> LENGTH: 4
<212> TYPE: PRT
<213> ORGANISM: Homo sapiens
```

```
<400> SEQUENCE: 11

Arg Ser Arg Lys
1

<210> SEQ ID NO 12
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with beta-glucose

<400> SEQUENCE: 12

Lys Thr Thr Lys Ser
1               5

<210> SEQ ID NO 13
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with per-acetylated alpha-N-
      acetylgalactosamine

<400> SEQUENCE: 13

Lys Thr Thr Lys Ser
1               5

<210> SEQ ID NO 14
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with alpha-N-acetylgalactosamine

<400> SEQUENCE: 14

Lys Thr Thr Lys Ser
1               5

<210> SEQ ID NO 15
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with per-acetylated beta-N-
      acetylglucosamine

<400> SEQUENCE: 15
```

Lys Thr Thr Lys Ser
1               5

<210> SEQ ID NO 16
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with beta-N-acetylglucosamine

<400> SEQUENCE: 16

Lys Thr Thr Lys Ser
1               5

<210> SEQ ID NO 17
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with peracetylated beta-glucose

<400> SEQUENCE: 17

Lys Thr Thr Lys Ser
1               5

<210> SEQ ID NO 18
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with beta-glucose

<400> SEQUENCE: 18

Lys Thr Thr Lys Ser
1               5

<210> SEQ ID NO 19
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with peracetylated alpha-N-
      acetylgalactoseamine

<400> SEQUENCE: 19

Lys Thr Thr Lys Ser

```
1               5
```

<210> SEQ ID NO 20
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with alpha-N-acetylgalactoseamine

<400> SEQUENCE: 20

```
Lys Thr Thr Lys Ser
1               5
```

<210> SEQ ID NO 21
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with peracetylated beta-N-
      acetylglucoseamine

<400> SEQUENCE: 21

```
Lys Thr Thr Lys Ser
1               5
```

<210> SEQ ID NO 22
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with beta-N-acetylglucosamine

<400> SEQUENCE: 22

```
Lys Thr Thr Lys Ser
1               5
```

<210> SEQ ID NO 23
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated alpha-N-
      acetylgalactoseamine
<220> FEATURE:
<221> NAME/KEY: CARBOHYD
<222> LOCATION: (3)..(3)
<223> OTHER INFORMATION: glycosylated with peracetylated alpha-N-
      acetylgalactoseamine

```
<400> SEQUENCE: 23

Lys Thr Thr Lys Ser
1               5

<210> SEQ ID NO 24
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with alpha-N-acetylgalactoseamine
<220> FEATURE:
<221> NAME/KEY: CARBOHYD
<222> LOCATION: (3)..(3)
<223> OTHER INFORMATION: glycosylated with alpha-N-acetylgalactoseamine

<400> SEQUENCE: 24

Lys Thr Thr Lys Ser
1               5

<210> SEQ ID NO 25
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated alpha-N-
      acetylgalactoseamine

<400> SEQUENCE: 25

Lys Thr Thr Lys Ser
1               5

<210> SEQ ID NO 26
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with alpha-N-acetylgalactoseamine

<400> SEQUENCE: 26

Lys Thr Thr Lys Ser
1               5

<210> SEQ ID NO 27
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
```

```
<222> LOCATION: (5)..(5)
<223> OTHER INFORMATION: glycosylated with beta-glucose

<400> SEQUENCE: 27

Lys Thr Thr Lys Ser
1               5

<210> SEQ ID NO 28
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-N-
      acetylglucoseamine

<400> SEQUENCE: 28

Lys Thr Thr Lys Ser
1               5

<210> SEQ ID NO 29
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with beta-N-acetylglucoseamine

<400> SEQUENCE: 29

Lys Thr Thr Lys Ser
1               5

<210> SEQ ID NO 30
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with beta-galactose

<400> SEQUENCE: 30

Lys Thr Thr Lys Ser
1               5

<210> SEQ ID NO 31
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with alpha-mannose
```

```
<400> SEQUENCE: 31

Lys Thr Thr Lys Ser
1               5

<210> SEQ ID NO 32
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated beta-glucose

<400> SEQUENCE: 32

Lys Ser Thr Lys Ser
1               5

<210> SEQ ID NO 33
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with beta-glucose

<400> SEQUENCE: 33

Lys Ser Thr Lys Ser
1               5

<210> SEQ ID NO 34
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated-beta-glucose

<400> SEQUENCE: 34

Lys Asn Thr Lys Ser
1               5

<210> SEQ ID NO 35
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with beta-glucose

<400> SEQUENCE: 35
```

Lys Asn Thr Lys Ser
1               5

<210> SEQ ID NO 36
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (1)..(1)
<223> OTHER INFORMATION: glycosylated with peracetylated beta-glucose

<400> SEQUENCE: 36

Asn Lys Thr Thr Lys Ser
1               5

<210> SEQ ID NO 37
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (1)..(1)
<223> OTHER INFORMATION: glycosylated with beta-glucose

<400> SEQUENCE: 37

Asn Lys Thr Thr Lys Ser
1               5

<210> SEQ ID NO 38
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with beta-maltose

<400> SEQUENCE: 38

Lys Thr Thr Lys Ser
1               5

<210> SEQ ID NO 39
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated beta-galactose

<400> SEQUENCE: 39

Lys Thr Thr Lys Ser
1               5

```
<210> SEQ ID NO 40
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (3)..(3)
<223> OTHER INFORMATION: glycosylated with peracetylated beta-galactose

<400> SEQUENCE: 40

Lys Thr Thr Lys Ser
1               5

<210> SEQ ID NO 41
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated beta-lactose

<400> SEQUENCE: 41

Lys Thr Thr Lys Ser
1               5

<210> SEQ ID NO 42
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-lactose

<400> SEQUENCE: 42

Lys Thr Thr Lys Ser
1               5

<210> SEQ ID NO 43
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated alpha-rhamnose

<400> SEQUENCE: 43

Lys Thr Thr Lys Ser
1               5

<210> SEQ ID NO 44
<211> LENGTH: 5
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated alpha-rhamnose

<400> SEQUENCE: 44

Lys Thr Thr Lys Ser
1               5

<210> SEQ ID NO 45
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (2)..(2)
<223> OTHER INFORMATION: glycosylated with peracetylated beta-cellobiose

<400> SEQUENCE: 45

Lys Thr Thr Lys Ser
1               5

<210> SEQ ID NO 46
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-cellobiose

<400> SEQUENCE: 46

Lys Thr Thr Lys Ser
1               5

<210> SEQ ID NO 47
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-xylose

<400> SEQUENCE: 47

Lys Thr Thr Lys Ser
1               5

<210> SEQ ID NO 48
<211> LENGTH: 5
<212> TYPE: PRT
<213> ORGANISM: Homo sapiens
<220> FEATURE:
```

```
<221> NAME/KEY: MOD_RES
<222> LOCATION: (1)..(1)
<223> OTHER INFORMATION: having an N-terminal palmitoyl
<220> FEATURE:
<221> NAME/KEY: CARBOHYD
<222> LOCATION: (5)..(5)
<223> OTHER INFORMATION: glycosylated with peracetylated beta-fucose

<400> SEQUENCE: 48

Lys Thr Thr Lys Ser
1               5
```

GLYCOPEPTIDE COMPOSITIONS AND USES THEREOF

CROSS REFERENCE TO RELATED APPLICATIONS

This application is a national stage application of PCT/CA2014/051190 filed on Dec. 9, 2014 under 35 U.S.C. 371, which claims the benefit of priority of U.S. Provisional Patent Application No. 61/914,309 filed Dec. 10, 2013, all of which are hereby incorporated by reference.

FIELD

The present disclosure relates to the glycosylation of oligopeptides consisting of between 5 and 6 amino acids for use in cosmetic and dermopharmaceutical compositions and applications.

BACKGROUND

The concerns of skin aging are of increasing importance to the fields of dermatology and cosmetic medicine. Skin aging is a complicated process caused in part by the reduction of Extracellular Matrix (ECM) components including collagen, elastin and fibronectin (Callaghan, T M and Wilhelm, K P (2008) Int J. Cosmet. Sci. 30:313-322). Type I collagen is the most abundant type of collagen and functions in structural integrity, cell adhesion and migration, tissue remodeling and wound healing (Trojanowska, M et al., (1998) J. Mol. Med. 76:266-267; Chiquet, M. et al., (1996) Biochem. Cell Biol. 74:737-744). In 1993 a pentapeptide (Lys-Thr-Thr-Lys-Ser also known as KTTKS SEQ ID NO: 1)) derived from the carboxyl-terminus of type I procollagen was shown to promote ECM production (Katayama, K et al., (1993) J. Biol. Chem. 268:9941-9944). In an in vitro model using human lung fibroblasts, the pentapeptide was found to significantly augment the ECM proteins through increased synthesis of collagen types I and III and fibronectin.

Although the aforementioned in vitro data demonstrated the pentapeptide's ability to stimulate collagen and fibronectin synthesis, its net charge posed a challenge to transcutaneous penetration. In order to enhance the peptides activity, stability and increase lipophilicity, Lintner et al. (Lintner (2003) U.S. Pat. No. 6,620,419) conjugated the pentapeptide to the 16-carbon fatty acid, palmitate, to create Palmitoyl KTTKS (Pal-KTTKS, SEQ ID NO: 2). This fatty acid modification resulted in more effective delivery across skin relative to KTTKS (SEQ ID NO: 1) alone (Lintner, K (2002) Ann Dermatol Venereol 129: 1S 105; Mas-Chamberlin, C et al., (2002) Ann Dermatol Venereol 129: 1S 456; Tsai, T C and Hantash, B M (2008) Clin Med 2:1-20). Palmitoyl-KTTKS (SEQ ID NO: 2) was one of the first oligopeptides to be developed as a cosmetic agent and is currently the active ingredient in the cosmetic agent Matrixyl™ (Sederma SAS). The Pal-KTTKS (SEQ ID NO: 2) has been formulated with a skin care active and a dermatologically acceptable carrier to form skin care compositions for topical treatment of skin (The Proctor and Gamble Company). The resulting compositions have been found to be advantageous for skin treatment particularly against the formation of wrinkles and against other skin aging effects (Robinson (2002) U.S. Pat. No. 6,492,326). The Pal-KTTKS (SEQ ID NO: 2) has been found to decrease fibroblast cell viability under certain conditions.

It is desirable to provide alternative oliogopeptides capable of promoting ECM protein production and secretion from fibroblasts.

SUMMARY

Generally, the present disclosure provides a 5 or 6 amino acid glycosylated oligopeptide having the sequence: Palmitoyl-X1-Lys-X2-X3-Lys-X4-OH, where: X1 is: absent, Ser having a glycosylated side chain, or Asn having a glycosylated side chain; X2 is: Thr, Thr having a glycosylated side chain, Asn having a glycosylated side chain, or Ser having a glycosylated side chain; X3 is: Thr, or Thr having a glycosylated side chain; X4 is: Ser, or Ser having a glycosylated side chain, where: at least one of X1, X2, X3 and X4 is an amino acid having a glycosylated side chain; where: each glycosylated side chain is, independently, glycosylated with a carbohydrate selected from the group consisting of: glucose, N-acetyl-glucosamine, galactose, N-acetyl-galactosamine, mannose, maltose, lactose, rhamnose, cellobiose, xylose, and fucose; and where: each hydroxyl group on the carbohydrate is, independently, OH or acetylated. The sequence of the glycosylated peptide is defined in SEQ ID NO: 3.

The hydroxyl groups on the carbohydrate may all be acetylated.

The hydroxyl groups on the carbohydrate may all not be acetylated.

The amino acid at X1 may be absent.

Preferably, at least one of the amino acids is glycosylated with maltose, glucose, galactose, or mannose.

The amino acid at X2 may be Thr having a glycosylated side chain. The glycosylated side chain may be glycosylated with glucose or maltose. The amino acids at X1, X3 and X4 may all be unglycosylated.

The amino acid at X4 may be Ser having a glycosylated side chain. The glycosylated side chain may be glycosylated with glucose or galactose. The amino acids at X1, X2 and X3 amino acids may all be unglycosylated.

In a specific example, there is provided a glycosylated oligopeptide having the sequence: Palmitoyl-Lys-Thr*-Thr-Lys-Ser-OH, wherein Thr* is threonine glycosylated with per-acetylated β-glucose. (SEQ ID NO: 4)

Another exemplary oligopeptide according to the present disclosure has sequence: Palmitoyl-Lys-Thr*-Thr-Lys-Ser-OH, wherein Thr* is threonine glycosylated with per-acetylated α-mannose. (SEQ ID NO: 5)

In another specific example, there is provided a glycosylated oligopeptide having the sequence: Palmitoyl-Lys-Thr*-Thr-Lys-Ser-OH, wherein Thr* is threonine glycosylated with per-acetylated β-maltose. (SEQ ID NO: 6)

In still another specific example, there is provided a glycosylated oligopeptide having the sequence: Palmitoyl-Lys-Thr-Thr-Lys-Ser*-OH, wherein Ser* is serine glycosylated with per-acetylated β-galactose. (SEQ ID NO: 7)

In yet another specific example, there is provided a glycosylated oligopeptide having the sequence: Palmitoyl-Lys-Thr-Thr-Lys-Ser*-OH, wherein Ser* is serine glycosylated with per-acetylated β-glucose. (SEQ ID NO: 8)

In a further specific example, there is provided a glycosylated oligopeptide having the sequence: Palmitoyl-Lys-Thr-Thr*-Lys-Ser-OH, wherein Thr* is threonine glycosylated with per-acetylated β-maltose (SEQ ID NO: 9).

In yet another specific example, there is provided a glycosylated oligopeptide having the sequence: Palmitoyl-Lys-Thr-Thr-Lys-Ser*-OH, wherein Ser* is serine glycosylated with per-acetylated β-maltose (SEQ ID NO: 10).

In another aspect, the present disclosure provides a cosmetic or dermopharmaceutical composition that includes at least one glycosylated oligopeptide as described above.

In another aspect, the present disclosure provides a method of increasing the secretion of an extracellular matrix protein by a cell in an individual. The method includes topically administering to the individual the composition described above. The extracellular matrix protein may be elastin, fibronectin, or collagen.

In still another aspect, the present disclosure provides a use of a glycosylated oligopeptide as described above for increasing the secretion of an extracellular matrix protein by a cell. The extracellular matrix protein may be elastin, fibronectin, or collagen.

In yet another aspect, the present disclosure provides a skin care composition that includes: (a) a safe and effective amount of a glycosylated oligopeptide as described above, (b) a safe and effective amount of at least one additional skin care active selected from the group consisting of: desquamatory actives, anti-acne actives, vitamin $B_3$ compounds, retinoids, di-, tri-, tetra-, penta- and hexa-peptides and derivatives thereof, hydroxy acids, radical scavengers, chelators, anti-inflammatory agents, topical anesthetics, tanning actives, skin lightening agents, anti-cellulite agents, flavonoids, antimicrobial actives, skin healing agents, antifungal actives, farnesol, phytantriol, allantoin, glucosamine, and mixtures thereof; and (c) a dermatologically acceptable carrier.

The peptides disclosed herein, alone or in combination with each other, can be: used in the form of a solution, a dispersion, an emulsion; encapsulated in a vector, such as a macro-, micro- or nano-capsule, a lyposome or a chylomicron; included in a macro-, micro- or nano-particle; included in a micro-sponge; or adsorbed on a powdered organic polymer, talc, bentonite or another mineral support.

The peptides disclosed herein, alone or in combination with each other, can be used in a galenic formulation; an oil-in-water emulsion; a water-in-oil emulsion; milk; a lotion; or a gelifying, thickening, tensioactive or emulsifying polymer, pomade, lotion, capillary, shampoo, soap, powder, stick, pencil, spray or body oil.

The peptides disclosed herein, alone or in combination with each other, can be used with any other ingredient conventionally used, such as: an extraction lipid, a synthesis lipid, a gelifying, thickening, tensioactive, or emulsifying polymer, a hydrosoluble or liposoluble active principle, a vegetables extract, a tissue extract, a marine extract, a solar filter, or an antioxidant.

The peptides disclosed herein, alone or in combination with each other, can be used in a cosmetic application to promote healing, hydration or for skin care, particularly against the formation or worsening of wrinkles, or against a consequence of natural or accelerated cutaneous aging (such as heliodermia, or pollution).

The peptides disclosed herein, alone or in combination with each other, may be used to prepare a cosmetic or dermopharmaceutical medicament. The peptides or medicaments thereof can be used to promote healing, hydration, or for skin care, particularly against the formation or worsening of wrinkles, or against a consequence of natural or accelerated cutaneous aging (such as heliodermia, or pollution).

The peptides disclosed herein, alone or in combination with each other, can be used with a number of additional skin care actives. Exemplary skin care activities include wound healing, reducing appearance of stretch marks, psoriasis, skin cancer, dermatitis, eczema.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1A:
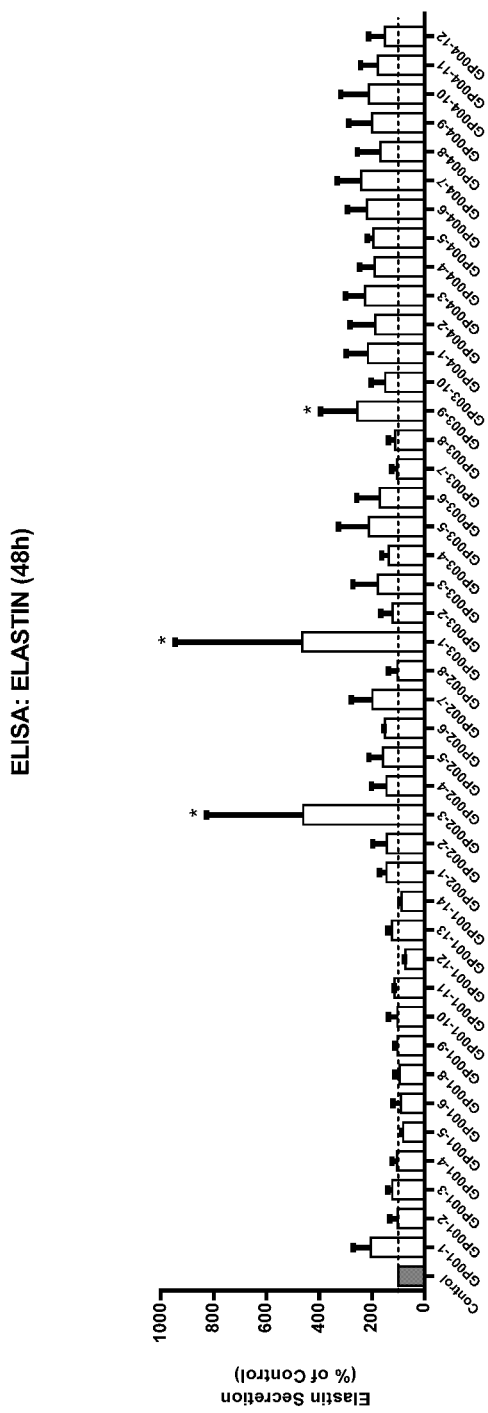
FIG. 1 is a graph showing the comparison of the efficacy of exemplary glycopeptides, on elastin secretion as % of control at 48 hours (A) and 72 hours (B) post-treatment of human dermal fibroblasts.

The post-translational modification of proteins and peptides by the covalent attachment of carbohydrates to specific side chains, called glycosylation, is emerging as a crucial process in modulating the function of proteins and peptides.

This process is a highly regulated within the cell as it varies with cell type, the site of glycosylation and the size of the carbohydrate chains (glycans). In humans, the most common sites for protein glycosylation occur on asparagine (N-glycosylation) and on serine and threonine residues (O-glycosylation) with the following sugars: Glucose (Glc), Fucose (Fuc), Galactose (Gal), Mannose (Man), N-acetylglucosamine (GlcNAc), N-acetylgalactosamine (GalNAc) and Sialic Acid (Sia). Glycosylation may also include glycosylation with the following sugars: lactose (Lac), rhamnose (Rha), cellobiose (Cel), and xylose (Xyl).

Glycosylation of proteins may increase protein binding and efficacy. For example, glycosylation of collagen allows the collagen to bind to the lecithin domain of membrane receptors, such as urokinase Plasminogen Activator Receptor-Associated Protein (uPARAP/Endo180). Glycosylation of a peptide may also increase stability of the resulting peptide.

Carbohydrates are one of the major constituents in the skin and play a role in skin homeostasis. Carbohydrates are found mostly on skin cells acting as ligands for receptors and conductors of external messages and for interacting with neighbouring cells. They may be involved in cell proliferation and differentiation, protein synthesis and may also be responsible for tissue structure and architecture.

In the aging process, there is an increased presence of reducing sugars. Glycation is a natural cellular process that occurs as a result of excess endogenous or exogenous reducing sugars covalently bonding to protein or lipid molecules. Glycation causes an increase in the cross-linking of extracellular proteins such as collagen, fibronectin and elastin making them biologically dysfunctional. Glycation enables formation of cross-links called Advanced Glycation End Products (AGEs) in the dermal ECM and disrupts the normal function of these biomolecules. Glycation happens in a haphazard way without the controlling action of an enzyme and is shown to be involved in wrinkle formation. It is believed in the art that reducing sugars were promoting the aging process. Glycosylation is not to be confused with the deleterious process of glycation.

Glycosylated peptides according to the present disclosure may increase the glycosylated peptides' stability, may increase their effectiveness in retarding the aging process, or both. Glycosylated peptides according to the present disclosure may, for example, reduce ECM protein degradation or induce ECM protein biosynthesis. Exemplary ECM proteins include: elastin, fibronectin and collagen.

Generally, the present disclosure provides glycosylated oligopeptides having the sequence Palmitoyl-X1-Lys-X2-X3-Lys-X4-OH, where: X1 is: absent, Ser having a glycosylated side chain, or Asn having a glycosylated side chain; X2 is: Thr, Thr having a glycosylated side chain, Asn having a glycosylated side chain, or Ser having a glycosylated side chain; X3 is: Thr, or Thr having a glycosylated side chain; X4 is: Ser, or Ser having a glycosylated side chain. At least one of X1, X2, X3 and X4 is an amino acid having a glycosylated side chain. Each glycosylated side chain is, independently, glycosylated with a carbohydrate selected from the group consisting of: glucose, N-acetyl-glucosamine, galactose, N-acetyl-galactosamine, mannose, maltose, lactose, rhamnose, cellobiose, xylose, and fucose. Each hydroxyl group on the carbohydrate is, independently, OH or acetylated. The sequence of the glycosylated peptide is defined in SEQ ID NO: 3.

In some examples, all the hydroxyl groups on the carbohydrate are acetylated. Oligosaccharides having acetylated hydroxyl groups may have improved permeability through cell membranes. Such improved permeability may improve delivery across skin.

Preferred oligopeptides according to the present disclosure have an N-terminal Palmitoyl group. Oligopeptides with N-terminal palmitoyl groups may have improved permeability through cell membranes. Such improved permeability may improve delivery across skin. Preferably, oligopeptides according to the present disclosure have five amino acids, where X1 is absent.

In some preferred oligopeptides, the X2 is Thr having a glycosylated side chain. The glycosylated side chain is glycosylated with glucose, mannose or maltose. The remaining amino acids are preferably unglycosylated.

In other preferred oligopeptides, the X3 is Thr having a glycosylated side chain. The glycosylated side chain is glycosylated with maltose. The remaining amino acids are preferably unglycosylated.

In still other preferred oligopeptides, the X4 is Ser having a glycosylated side chain. The glycosylated side chain is glycosylated with glucose, galactose or maltose. The remaining amino acids are preferably unglycosylated.

One exemplary oligopeptide according to the present disclosure has the sequence: Palmitoyl-Lys-Thr*-Thr-Lys-Ser-OH, wherein Thr* is threonine glycosylated with per-acetylated β-glucose. (SEQ ID NO: 4)

Another exemplary oligopeptide according to the present disclosure has sequence: Palmitoyl-Lys-Thr*-Thr-Lys-Ser-OH, wherein Thr* is threonine glycosylated with per-acetylated α-mannose. (SEQ ID NO: 5)

Still another exemplary oligopeptide according to the present disclosure has sequence: Palmitoyl-Lys-Thr*-Thr-Lys-Ser-OH, wherein Thr* is threonine glycosylated with per-acetylated β-maltose. (SEQ ID NO: 6)

Yet another exemplary oligopeptide according to the present disclosure has sequence: Palmitoyl-Lys-Thr-Thr-Lys-Ser*-OH, wherein Ser* is serine glycosylated with per-acetylated β-galactose. (SEQ ID NO: 7)

A still further exemplary oligopeptide according to the present disclosure has sequence: Palmitoyl-Lys-Thr-Thr-Lys-Ser*-OH, wherein Ser* is serine glycosylated with per-acetylated β-glucose. (SEQ ID NO: 8)

In a further specific example, there is provided a glycosylated oligopeptide having the sequence: Palmitoyl-Lys-Thr-Thr*-Lys-Ser-OH, wherein Thr* is threonine glycosylated with per-acetylated β-maltose (SEQ ID NO: 9).

In yet another specific example, there is provided a glycosylated oligopeptide having the sequence: Palmitoyl-Lys-Thr-Thr-Lys-Ser*-OH, wherein Ser* is serine glycosylated with per-acetylated β-maltose (SEQ ID NO: 10).

Glycosylated oligopeptides according to the present disclosure, such as the exemplary glycosylated oligopeptides listed above, may show an enhanced efficacy, reduced toxicity, or both in comparison to unglycosylated Pal-KTTKS (SEQ ID NO: 2).

Enhanced efficacy, in the context of the present disclosure, refers to greater induction of elastin, fibronectin or total collagen secretion in human dermal fibroblast cultures in vitro, when compared to unglycosylated Pal-KTTKS (SEQ ID NO: 2), as measured using the following kits: Fibronectin (Takara, MK115), Elastin (Uscn Life Science Inc., E91337Hu) and Total Collagen (Chondrex Inc., 9062).

In order for formulations that are used as a skin care product to be effective, the glycosylated peptide must, preferably, be stable in formula, be substantially absorbable into the skin, and be biologically active at the target.

The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The term "sagging" as used herein means the laxity, slackness, or the like condition of skin that occurs as a result of loss of, damage to, alterations to, and/or abnormalities in dermal elastin.

The terms "smoothing" and "softening" as used herein mean altering the surface of the keratinous tissue such that its tactile feel is improved.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The glycosylated peptides according to the presently disclosure may be useful for therapeutically regulating visible and/or tactile discontinuities in mammalian skin, including discontinuities in skin texture and color. For example, the apparent diameter of pores decreases, the apparent height of tissue immediately proximate to pore openings approaches that of the interadnexal skin, the skin tone/color becomes more uniform, and/or the length, depth, and/or other dimension of lines and/or wrinkles are decreased.

The glycosylated peptides according to the presently disclosure may be also useful for regulating the condition of skin and especially for regulating keratinous tissue condition. Regulation of skin condition, namely mammalian and in particular human skin condition, is often required due to conditions which may be induced or caused by factors internal and/or external to the body. Examples include: environmental damage, radiation exposure (including ultraviolet radiation), chronological aging, menopausal status (e.g., post-menopausal changes in skin), stress, diseases, etc. For instance, "regulating skin condition" includes prophylactically regulating and/or therapeutically regulating skin condition, and may involve one or more of the following benefits: thickening of skin (i.e., building the epidermis and/or dermis and/or sub-dermal (e.g., subcutaneous fat or muscle) layers of the skin and where applicable the keratinous layers of the nail and hair shaft) to reduce skin atrophy, increasing the convolution of the dermal-epidermal border (also known as the rete ridges), preventing loss of skin elasticity (loss, damage and/or inactivation of functional skin elastin) such as elastosis, sagging, loss of skin recoil from deformation; non-melanin skin discoloration such as under eye circles, blotching (e.g., uneven red coloration due to, e.g., rosacea) (hereinafter referred to as "red blotchiness"), sallowness (pale color), discoloration caused by telangiectasia or spider vessels.

As used herein, prophylactically regulating skin condition includes delaying, minimizing and/or preventing visible and/or tactile discontinuities in skin (e.g., texture irregularities in the skin which may be detected visually or by feel).

As used herein, therapeutically regulating skin condition includes ameliorating, e.g., diminishing, minimizing and/or effacing, discontinuities in skin.

The glycosylated peptides according to the present disclosure may also be useful for improving skin appearance and/or feel. For example, compositions according to the present disclosure may be useful for regulating the appearance of skin condition by providing an immediate visual improvement in skin appearance following application of the composition to the skin. Generally speaking, compositions of the present disclosure which further contain particulate materials will be most useful for providing the immediate visual improvement.

The compositions of the present disclosure may provide additional benefits, including stability, absence of significant (consumer-unacceptable) skin irritation and good aesthetics.

The compositions of the present disclosure are stable. The ingredients used herein, including the glycosylated peptide according to the present disclosure are stable in the composition and are compatible with each other and with the other skin care actives such as niacinamide, phytantriol, farnesol, bisabolol, and salicylic acid. Therefore, the compositions containing the combination of oligopeptides in conjunction with an additional skin care active, such as niacinamide, are capable of providing additive and/or synergistic skin benefits. Additionally, the resulting skin care composition has good product stability and a reasonably long shelf-life.

The resulting compositions containing a glycosylated peptide according to the present disclosure in combination with at least one additional skin care active have good aesthetics. Examples of good aesthetics include compositions, such as luxurious creams and lotions, that (i) are light and nongreasy, (ii) have a smooth, silky feel upon the skin, (iii) spread easily, and/or (iv) absorb quickly. Other examples of good aesthetics include compositions that have a consumer acceptable appearance (i.e. no unpleasant odor or discoloration present), and provide good skin feel.

In preferred examples, skin care products include from about 0.01% to about 50% of the glycosylated peptide, by weight of the composition. In more preferred examples, the skin care products include from about 0.05% to about 20%, of the glycosylated peptide, by weight of the composition. In even more preferred examples, the skin care products include from about 0.1% to about 10%, of the glycosylated peptide, by weight of the composition.

The glycosylated oligopeptides of the present disclosure may be formulated with at least one additional component. Where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present disclosure. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

Farnesol

Topical compositions of the present disclosure may contain a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the compositions of the present disclosure, the composition preferably contains from about 0.001% to about 50%, by weight of the composition, more preferably from about 0.01% to about 20%, even more preferably from about 0.1% to about 15%, even more preferably from about 0.1% to about 10%, still more preferably from about 0.5% to about 5%, and still more preferably from about 1% to about 5% of farnesol.

Phytantriol

The topical compositions of the present disclosure may contain a safe and effective amount of phytantriol. Phytantriol is the common name for the chemical known as 3,7,11,15, tetramethylhexadecane-1,2,3, -triol. Phytantriol is commercially available from BASF (1609 Biddle Avenue, Whyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

In the compositions of the present disclosure, the phytantriol preferably is included in an amount from about 0.001% to about 50% by weight of the composition, more preferably from about 0.01% to about 20%, even more preferably from about 0.1% to about 15%, even more preferably from about 0.2% to about 10%, still more preferably from about 0.5% to about 10%, and still more preferably from about 1% to about 5%.

Desquamation Actives

A safe and effective amount of a desquamation active may be added to the compositions of the present disclosure, more preferably from about 0.1% to about 10%, even more preferably from about 0.2% to about 5%, also preferably from about 0.5% to about 4%, by weight of the composition. Desquamation actives enhance the skin appearance benefits of the present disclosure. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

Anti-Acne Actives

The compositions of the present disclosure may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980, issued to McAtee et al, on Mar. 4, 1997.

Anti-Wrinkle Actives/Anti-Atrophy Actives

The compositions of the present disclosure may further contain a safe and effective amount of one or more antiwrinkle actives or anti-atrophy actives. Exemplary antiwrinkle/anti-atrophy actives suitable for use in the compositions of the present disclosure include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds and retinoids which enhance the keratinous tissue appearance benefits of the present disclosure, especially in regulating keratinous tissue condition, e.g., skin condition.

a) Vitamin $B_3$ Compounds

The compositions of the present disclosure may contain a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997). When vitamin $B_3$ compounds are present in the compositions of the instant disclosure, the compositions preferably contain from about 0.01% to about 50%, more preferably from about 0.1% to about 10%, even more preferably from about 0.5% to about 10%, and still more preferably from about 1% to about 5%, still more preferably from about 2% to about 5%, by weight of the composition, of the vitamin $B_3$ compound.

As used herein, "vitamin $B_3$ compound" means a compound having the formula:

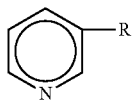

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

b) Retinoids

The compositions of the present disclosure may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl6-[2-(4,4-dimethylthiochroman-6-yl)-ethynyl]nicotinate). Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The compositions according to this disclosure may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Where the compositions of the present disclosure contain both a retinoid and a Vitamin $B_3$ compound, the retinoid is preferably used in the above amounts, and the vitamin $B_3$ compound is preferably used in an amount of from or about 0.1% to or about 10%, more preferably from or about 2% to or about 5%.

(c) Hydroxy Acids

The compositions of the present disclosure may contain a safe and effective amount of a Hydroxy Acid. Preferred hydroxy acids for use in the compositions of the present disclosure include salicylic acid and salicylic acid derivatives. When present in the compositions of the present disclosure, salicylic acid is preferably used in an amount of from about 0.01% to about 50%, more preferably from about 0.1% to about 20%, even more preferably from about 0.1% to about 10%, still more preferably from about 0.5% to about 5%, and still more preferably from about 0.5% to about 2%.

Peptides

Additional peptides, including but not limited to, di-, tri-, and tetrapeptides and derivatives thereof, may be included in the compositions of the present disclosure in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine (beta-ala-his). Suitable tripeptides for use herein include, gly-his-lys, arg-lys-arg, his-gly-gly. Preferred tripeptides and derivatives thereof include palmitoyl-gly-his-lys, which may be purchased as Biopeptide CL® (100 ppm of palmitoyl-gly-his-lys commerically available from Sederma, France); Peptide CK (arg-lys-arg); Peptide CK+(ac-arg-lys-arg-$NH_2$); and a copper derivative of his-gly-gly sold commercially as lamin, from Sigma (St. Louis, Mo.). Suitable tetrapeptides for use herein include Peptide E, arg-ser-arg-lys (SEQ ID NO: 11).

Preferably, the additional peptide is selected from palmitoyl-gly-his-lys, beta-ala-his, their derivatives, and combinations thereof. More preferably, the additional peptide is selected from palmitoyl-gly-his-lys, their derivatives, and combinations thereof.

When included in the present compositions, the additional peptides are preferably included in amounts of from about $1 \times 10^{-6}\%$ to about 10%, more preferably from about $1 \times 10^{-6}\%$ to about 0.1%, even more preferably from about $1 \times 10^{-5}\%$ to about 0.01%, by weight of the composition. In certain embodiments which include the peptide, Carnosine®, the compositions preferably contain from about 0.1% to about 5%, by weight of the composition, of such peptides. In other embodiments wherein the peptide-containing composition Biopeptide CL® is included, the resulting composition preferably contains from about 0.1% to about 10%, by weight of the composition, of the Biopeptide CL®.

Anti-Oxidants/Radical Scavengers

The compositions of the present disclosure may include a safe and effective amount of an anti-oxidant/radical scavenger. The anti-oxidant/radical scavenger is especially useful for providing protection against UV radiation which can cause increased scaling or texture changes in the stratum corneum and against other environmental agents which can cause skin damage.

A safe and effective amount of an anti-oxidant/radical scavenger may be added to the compositions of the subject disclosure, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilorate, nordihydroguaiaretic acid, bioflavonoids, curcumin, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present disclosure is described in U.S. Pat. No. 4,847,071, issued on Jul. 11, 1989 to Donald L. Bissett, Rodney D. Bush and Ranjit Chatterjee.

Chelators

The compositions of the present disclosure may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

A safe and effective amount of a chelating agent may be added to the compositions of the subject disclosure, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the present disclosure are furildioxime, furilmonoxime, and derivatives thereof.

Flavonoids

The compositions of the present disclosure may optionally contain a flavonoid compound. Flavonoids are broadly disclosed in U.S. Pat. Nos. 5,686,082 and 5,686,367, both of which are herein incorporated by reference. Flavonoids suitable for use in the present disclosure are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone,2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. More preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in compositions according to the present disclosure at concentrations of from about 0.01% to about 20%, more preferably from about 0.1% to about 10%, and still more preferably from about 0.5% to about 5%.

Anti-Inflammatory Agents

A safe and effective amount of an anti-inflammatory agent may be added to the compositions of the present disclosure, preferably from about 0.1% to about 10%, more preferably from about 0.5% to about 5%, of the composition. The anti-inflammatory agent enhances the skin appearance benefits of the present disclosure, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in a composition according to the present disclosure include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are more preferred.

Finally, so-called "natural" anti-inflammatory agents are useful in methods of the present disclosure. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present disclosure may also contain a safe and effective amount of an anti-cellulite agent. Suitable agents may include, but are not limited to, xanthine compounds (e.g., caffeine, theophylline, theobromine, and aminophylline).

Topical Anesthetics

The compositions of the present disclosure may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Actives

The compositions of the present disclosure may contain a tanning active. When present, it is preferable that the compositions contain from about 0.1% to about 20%, more preferably from about 2% to about 7%, and still more preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

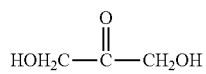

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See The Merck Index, Tenth Edition, entry 3167, p. 463 (1983), and "Dihydroxyacetone for Cosmetics", E. Merck Technical Bulletin, 03-304 110, 319 897, 180 588.

Skin Lightening Agents

The compositions of the present disclosure may contain a skin lightening agent. When used, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the PCT publication No. 95/34280, in the name of Hillebrand, corresponding to PCT Application No. U.S. Ser. No. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication Ser. No. 95/23780, published Sep. 8, 1995.

Skin Soothing and Skin Healing Actives

The compositions of the present disclosure may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed.

a) Bisabolol

The topical compositions of the present disclosure may also contain a safe and effective amount of bisabolol. Bisabolol is a naturally occurring unsaturated monocyclic terpene alcohol having the following structure

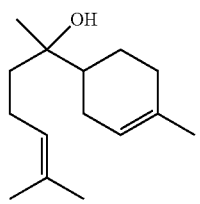 [SMILES: CC(C)=CCCC(C)(O)C1CC=C(C)CC1]

It is the primary active component of chamomile extract/oil. Bisabolol can be synthetic (d,1-alpha-isomer or (+/−)-alpha-isomer) or natural ((−)-alpha-isomer) in origin and can be used as essentially pure compounds or mixtures of compounds (e.g., extracts from natural sources such as chamomile). The alpha form of bisabolol (á-bisabolol) is used in a variety of cosmetic products as a skin conditioning or soothing agent. As used herein, "bisabolol" includes chamomile extract or oil and any isomers and tautomers of such. Suitable bisabolol compounds are commercially available as a natural material from Dragoco (Totowa, N.J.) under the product name alpha-bisabolol natural and as a synthetic material from Fluka (Milwaukee, Wis.) under the product name alpha-bisabolol.

In the compositions of the present disclosure, the composition preferably contains from about 0.001% to about 50%, by weight of the composition, more preferably from about 0.01% to about 20%, even more preferably from about 0.01% to about 15%, and still more preferably from about 0.1% to about 10%, of bisabolol, even more preferably from about 0.1% to about 5%.

Antimicrobial and Antifungal Actives

The compositions of the present disclosure may contain an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and still more preferably from about 0.05% to about 2%.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Actives

Exposure to ultraviolet light can result in excessive scaling and texture changes of the stratum corneum. Therefore, the compositions of the present disclosure may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional organic sunscreen actives are suitable for use herein. Sagarin, et al., at Chapter VIII, pages 189 et seq., of *Cosmetics Science and Technology* (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one), terephthalylidene dicamphor sulfonic acid and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the compositions include 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoicacid, octocrylene and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N, N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor (SPF).

Particulate Material

The compositions of the present disclosure may contain a particulate material, preferably a metallic oxide. These particulates can be coated or uncoated, charged or uncharged. Charged particulate materials are disclosed in U.S. Pat. No. 5,997,887, to Ha, et al., incorporated herein by reference. Particulate materials useful herein include; bismuth oxychloride, iron oxide, mica, mica treated with barium sulfate and $TiO_2$, silica, nylon, polyethylene, talc, styrene, polyproylene, ethylene/acrylic acid copolymer, sericite, aluminum oxide, silicone resin, barium sulfate, calcium carbonate, cellulose acetate, titanium dioxide, polymethyl methacrylate, and mixtures thereof.

Inorganic particulate materials, e.g., $TiO_2$, ZnO, or $ZrO_2$ are commercially available from a number of sources. One example of a suitable particulate material contains the material available from U.S. Cosmetics (TRONOX $TiO_2$ series, SAT-T CR837, a rutile $TiO_2$). Preferably, particulate materials are present in the composition in levels of from about 0.01% to about 2%, more preferably from about 0.05% to about 1.5%, still more preferably from about 0.1% to about 1%, by weight of the composition.

Conditioning Agents

The compositions of the present disclosure may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from urea, guanidine, sucrose polyester, panthenol, dexpanthenol, allantoin, and combinations thereof.

Structuring Agents

The compositions hereof, and especially the emulsions hereof, may contain a structuring agent. Structuring agents are particularly preferred in the oil-in-water emulsions of the present disclosure. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions contain from about 0.1% to about 20%, more preferably from about 0.1% to about 10%, still more preferably from about 0.5% to about 9%, of one or more structuring agents.

Preferred structuring agents are those having an HLB of from about 1 to about 8 and having a melting point of at least about 45° C. Suitable structuring agents are those selected from saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present disclosure are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present disclosure are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

Thickening Agent (Including Thickeners and Gelling Agents)

The compositions of the present disclosure can contain one or more thickening agents, preferably from about 0.1% to about 5%, more preferably from about 0.1% to about 4%, and still more preferably from about 0.25% to about 3%, by weight of the composition.

Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present disclosure are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaerytritol. These copolymers are known as acrylates/$C_{10}$-$C_{30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/$C_{10}$-$C_{30}$ alkyl acrylate crosspolymers, and mixtures thereof.

b) Crosslinked Polyacrylate Polymers

The compositions of the present disclosure can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

c) Polyacrylamide Polymers

The compositions of the present disclosure can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

d) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present disclosure include a thickening agent selected from carboxylic acid polymers, crosslinked polyacrylate polymers, polyacrylamide polymers, and mixtures thereof, more preferably selected from carboxylic acid polymers, polyacrylamide polymers, and mixtures thereof.

Dermatologically-Acceptable Carrier

The topical compositions of the present disclosure also contain a dermatologically acceptable carrier. The phrase "dermatologically-acceptable carrier", as used herein, means that the carrier is suitable for topical application to the keratinous tissue, has good aesthetic properties, is compatible with the actives of the present disclosure and any other components, and will not cause any untoward safety or toxicity concerns. A safe and effective amount of carrier is from about 50% to about 99.99%, preferably from about 80% to about 99.9%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Oil-in-water emulsions are especially preferred.

Emulsions according to the present disclosure generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic.

Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Preferred water-in-silicone and oil-in-water emulsions are described in greater detail below.

A) Water-in-Silicone Emulsion

Water-in-silicone emulsions contain a continuous silicone phase and a dispersed aqueous phase.

(1) Continuous Silicone Phase

Preferred water-in-silicone emulsions of the present disclosure contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the retinoid. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in PCT Application WO 97/21423, published Jun. 19, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and still more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(2) Dispersed Aqueous Phase

The topical compositions of the present disclosure contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present disclosure will typically contain from about 25% to about 90%, preferably from about 40% to about 80%, more preferably from about 60% to about 80%, water in the dispersed aqueous phase by weight of the composition.

(3) Emulsifier for Dispersing the Aqueous Phase

The water-in-silicone emulsions of the present disclosure preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present disclosure, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

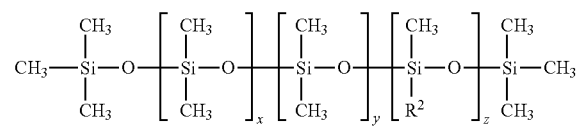

wherein R is $C_1$-$C_{30}$ straight, branched, or cyclic alkyl and $R^2$ is selected from the group consisting of

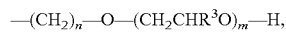

and

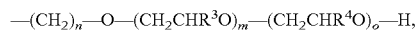

wherein n is an integer from 3 to about 10; $R^3$ and $R^4$ are selected from the group consisting of H and $C_1$-$C_6$ straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

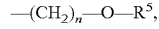

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant $C_2$-$C_{30}$ straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to SanoGueira, published Aug. 30, 1989; G. H. Dahms, et al., "New Formulation Possibilities Offered by Silicone Copolyols," *Cosmetics & Toiletries*, vol. 110, pp. 91-100, March 1995; M. E. Carlotti et al., "Optimization of W/O-S Emulsions And Study Of The Quantitative Relationships Between Ester Structure And Emulsion Properties," *J. Dispersion Science And Technology*, 13(3), 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," *Provisional Communication International Journal of Cosmetic Science*, 12, 135-139 (1990); and D. G. Krzysik et al., "A New Silicone Emulsifier For Water-in-Oil Systems," *Drug and Cosmetic Industry*, vol. 146(4) pp. 28-81 (April 1990).

Among the non-silicone-containing emulsifiers useful herein are various non-ionic and anionic emulsifying agents such as sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

B) Oil-in-Water Emulsions

Other preferred topical carriers include oil-in-water emulsions, having a continuous aqueous phase and a hydrophobic, water-insoluble phase ("oil phase") dispersed therein. Examples of suitable oil-in-water emulsion carriers are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(1) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions contain from about 0.5% to about 20%, more preferably from about 1% to about 10%, even more preferably from about 1% to about 5%, by weight of the composition, of a structuring agent.

The preferred structuring agents of the present disclosure include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present disclosure are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

(2) Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from non-ionic surfactants. Among the nonionic surfactants that are useful herein are those that can be broadly defined as condensation products of long chain alcohols, e.g. $C_{8-30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a $C_{10-30}$ alkyl group, X is $-OCH_2CH_2-$ (i.e. derived from ethylene glycol or oxide) or $-OCH_2CHCH_3-$ (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a $C_{10-30}$ alkyl group, X is $-OCH_2CH_2-$ (i.e. derived from ethylene glycol or oxide) or $-OCH_2CHCH_3-$ (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a $C_{10-30}$ alkyl group, X is $-OCH_2CH_2-$ (i.e. derived from ethylene glycol or oxide) or $-OCH_2CHCH_3-$ (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10-30 alkyl groups, X is $-OCH_2CH_2$ (i.e. derived from ethylene glycol or oxide) or $-OCH_2CHCH_3-$ (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$-$C_4$ alkyl, 2-hydroxyethyl, 2-hydroxy-propyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_1$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO-$ moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of C1-C30 fatty acid esters of $C_1$-C30 fatty alcohols, alkoxylated ethers of C1-C30 fatty alcohols, polyglyceryl esters of $C_1$-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. See, e.g., McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. No. 5,151,209; U.S. Pat.

No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's Deterrents & Emulsifiers*, (North American edition 1979) M.C. Publishing Co.; and Schwartz, et al., *Surface Active Agents, Their Chemistry and Technology*, New York: Interscience Publishers, 1949; which descriptions are incorporated herein by reference. The cationic surfactants useful herein include cationic ammonium salts such as those having the formula:

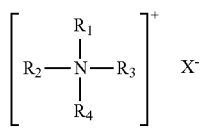

wherein $R_1$, is an alkyl group having from about 12 to about 30 carbon atoms, or an aromatic, aryl or alkaryl group having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Still more preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH-(CH_2)_n$, wherein $R_5$ is an alkyl group having from about 12 to about 22 carbon atoms, and n is an integer from about 2 to about 6, more preferably from about 2 to about 4, and still more preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintain and to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

R—SO$_3$-M wherein R$_1$ is chosen from the group including a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present disclosure are those which are broadly described as derivatives of aliphatic secondary and tertiary amines in which the aliphatic radical can be straight or branched chain and wherein one of the aliphatic substituents contains from about 8 to about 22 carbon atoms (preferably C$_8$-C$_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH$_2$)$_m$CO$_2$M]$_2$ and RNH (CH$_2$)$_m$CO$_2$M wherein m is from 1 to 4, R is a C$_8$-C$_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528, 378, which is incorporated herein by reference in its entirety. Other examples of useful amphoterics include phosphates, such as coamidopropyl PG-dimonium chloride phosphate (commercially available as Monaquat PTC, from Mona Corp.).

Other amphoteric or zwitterionic surfactants useful herein include betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH (CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(3) Water

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions according to the present disclosure, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients are known and may be used herein. Sagarin, *Cosmetics Science and Technology,* 2nd Edition, Vol. 1, pp. 32-43 (1972), incorporated herein by reference, contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Lotions and creams according to the present disclosure generally contain a solution carrier system and one or more emollients. Lotions and creams typically contain from about 1% to about 50%, preferably from about 1% to about 20%, of emollient; from about 50% to about 90%, preferably from about 60% to about 80%, water; and the pentapeptide and/or pentapeptide derivative and the additional skin care active (or actives) in the above described amounts. Creams are generally thicker than lotions due to higher levels of emollients or higher levels of thickeners.

Ointments of the present disclosure may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, *Cosmetics, Science and Technology*, 2nd Edition, Vol. 1, pp. 72-73 (1972), incorporated herein by reference, and/or an emollient. For example, an ointment may contain from about 2% to about 10% of an emollient; from about 0.1% to about 2% of a thickening agent; and the pentapeptide and/or pentapeptide derivative and the additional skin care active (or actives) in the above described amounts.

Compositions according to the present disclosure useful for cleansing ("cleansers") are formulated with a suitable carrier, e.g., as described above, and preferably contain, in addition to the pentapeptide and/or pentapeptide derivative and the additional skin care active (or actives) in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers*, North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present disclosure include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in PCT Application, WO 96/33689, to Canter, et al., published on Oct. 31, 1996 and U.K. Patent, GB 2274585, issued on Aug. 3, 1994.

Composition Preparation

The compositions useful for the methods of the present disclosure are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present disclosure are useful for regulating mammalian skin condition. Such regulation of keratinous tissue conditions can include prophylactic and therapeutic regulation. For example, such regulating methods are directed to thickening keratinous tissue (i.e., building the epidermis and/or dermis layers of the skin and where applicable the keratinous layers of the nail and hair shaft) and preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallowness of mammalian skin, preventing and/or retarding sagging of mammalian skin, softening and/or smoothing lips, hair and nails of a mammal, preventing and/or relieving itch of mammalian skin, regulating skin texture (e.g. wrinkles and fine lines), and improving skin color (e.g. redness, freckles).

Regulating keratinous tissue condition involves topically applying to the keratinous tissue a safe and effective amount of a composition of the present disclosure. The amount of the composition which is applied, the frequency of application and the period of use will vary widely depending upon the level of pentapeptides and/or pentapeptide derivatives and the additional skin care active or actives, in a given composition and the level of regulation desired, e.g., in light of the level of keratinous tissue damage present or expected to occur.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present disclosure can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 1 mg/$cm^2$ to about 2 mg/$cm^2$.

Regulating keratinous tissue condition is preferably practiced by applying a composition in the form of a skin lotion, cream, gel, foam, ointment, paste, emulsion, spray, conditioner, tonic, cosmetic, lipstick, foundation, nail polish, after-shave, or the like which is preferably intended to be left on the skin or other keratin structure for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, still more preferably for at least several hours, e.g., up to about 12 hours. Any part of the external portion of the face, hair, and/or nails can be treated, e.g., face, lips, under-eye area, eyelids, scalp, neck, torso, arms, hands, legs, feet, fingernails, toenails, scalp hair, eyelashes, eyebrows, etc. The composition can be applied with the fingers or with an implement or device (e.g., pad, cotton ball, applicator pen, spray applicator, and the like).

Another approach to ensure a continuous exposure of the skin to at least a minimum level of the the pentapeptide and/or pentapeptide derivative and the additional skin care active (or actives) is to apply the compound by use of a patch applied, e.g., to the face. Such an approach is particularly useful for problem skin areas needing more intensive treatment (e.g., facial crows feet area, frown lines, under eye area, and the like). The patch can be occlusive, semi-occlusive or non-occlusive and can be adhesive or non-adhesive. The pentapeptide and/or pentapeptide derivative and the additional skin care active (or actives) composition can be contained within the patch or be applied to the skin prior to application of the patch. The patch can also include additional actives such as chemical initiators for exothermic reactions such as those described in U.S. Pat. Nos. 5,821,250, 5,981,547, and 5,972,957 to Wu, et al. The patch is preferably left on the skin for a period of at least about 5 minutes, more preferably at least about 15 minutes, more preferably still at least about 30 minutes, even more preferably at least about 1 hour, still more preferably at night as a form of night therapy.

In the following description, for purposes of explanation, numerous details are set forth in order to provide a thorough understanding of the examples. However, it will be apparent to one skilled in the art that these specific details are not required.

EXAMPLES

Materials and Methods

General Synthetic Procedure for Glycosylated Pal-KTTKS Derivatives

Four groups of similarly modified pentapeptides were made based on the Pal-KTTKS sequence by glycosylating all possible sites with various sugars (Glc, Gal, GlcNAc, GalNAc, Man, Mal, Lac, Rha, Cel, Xyl, Fuc) in both peracetylated and deacetylated forms. These synthesized compounds were subsequently tested for toxicity and biological activity by examining elastin, fibronectin and total collagen secretion on human dermal fibroblast cultures in vitro and elastin secretion and histology in an in vitro 3D model of human skin (comprised of human epidermal keratinocytes and human dermal fibroblasts). For the four groups of similarly modified peptides made, chemical identity was confirmed by HPLC and Mass Spectrometry.

Group 1 modifications involved glycosylation with glucose, N-acetylglucosamine, galactose, N-acetylgalactosamine, or a combination thereof, in peracetylated or deacetylated forms, on either one or both of the two intermediate Threonines in the Pal-KTTKS sequence.

Group 2 modifications involved glycosylation with glucose, N-acetylglucosamine, galactose, N-acetylgalactosamine, in peracetylated or deacetylated form, on the terminal serine in the Pal-KTTKS sequence.

Group 3 modifications involved glycosylation with mannose or maltose, in peracetylated or deacetylated forms, on the first Threonine in the Pal-KTTKS sequence. Group 3 modifications also included a serine substitution for the first threonine in the Pal-KTTKS sequence, where the serine is glycosylated with glucose, in peracetylated or deacetylated form. Group 3 modifications also included an asparagine substitution for the first threonine in the Pal-KTTKS sequence, where the asparagine is glycosylated with glucose, in either peracetylated or deacetylated form. Group 3 modifications also included the addition of an asparagine amino acid at the N-terminus of the Pal-KTTKS sequence, where the asparagine is glycosylated with glucose, in either peracetylated or deacetylated form.

Group 4 modifications involved glycosylation with galactose, maltose, lactose, rhamnose, cellobiose, xylose or fucose, in peracetylated forms, on the first or second Threonine in the Pal-KTTKS sequence, or on the terminal serine in the Pal-KTTKS sequence.

All chemical reagents were obtained from commercial suppliers as reagent or HPLC grade and used without further purification. Dichloromethane (DCM) was dried via distillation from calcium hydride ($CaH_2$). Unless otherwise specified, all reactions were conducted at room temperature. All non-glycosylated Fmoc-protected amino acids used for glycopeptide synthesis were obtained from Novabiochem (EMD Millipore). All glycosylated Fmoc-protected amino acids (glycoamino acids or glycosylated amino acids) used for glycopeptide synthesis are commercially available from Sussex Research Laboratories Inc. (Ottawa, Canada) (<http://www.sussex-research.com/products/glycoamino-acids/all-gly-coamino-acids/>). Pre-loaded resin (H-L-Ser (t-Bu)-2-Cl-Trityl resin) was purchased from Matrix Innovation (Quebec, Canada) Standard resin (Novabiochem 2-Chlorotrityl Chloride resin) was obtained from EMD Millipore. Palmitic acid (purity >99%) was purchased from Sigma Aldrich.

Reversed-phase high pressure liquid chromatography (RP-HPLC) was performed on a Gilson chromatograph outfitted with an 805 Manometric module (max pressure 60 MPa), 811C Dynamic Mixer, 305 Pump and UV/VIS-155 Detector using a Phenomenex Luna C18 column: particle size 5 µm, analytical column 250×4.60 mm. Gradients consisted of mobile phases A and B (water/TFA (100/0.1) and acetonitrile/TFA (100/0.1), respectively. The glycopeptides were eluted from the column via a linear gradient of 2-70% mobile phase B over 40 minutes at flow rate of 1 mL/min with UV detection at 214 nm. Preparative HPLC was carried out on a Gilson chromatograph (805 Manometric module, max pressure 60 MPa; 811C Dynamic Mixer, 305 Pump, UV/VIS-155 Detector) using a Phenomenex Luna C18 column: particle size 10 µm, semi-preparative column 250×21.20 mm). Mobile phases A and B consisted of (water/TFA (100/0.1) and acetonitrile/TFA (100/0.1), respectively. Glycopeptides were separated from impurities via a linear gradient of 2-70% mobile phase B in 35 minutes at flow rate of 10 mL/min with UV detection at 214 nm.

Analysis of peptide samples was performed on an electrospray ionization mass spectrometry (ESI-MS) using a Micromass ZQ Single Quadrupole mass spectrometer.

General Procedure for the Synthesis of Per-Acetylated Threonine Glycosylated Oligopeptides Glycopeptides were synthesized on a CS Bio CS136XT automated synthesizer using a standard Fmoc solid phase peptide synthesis (SPPS) methodology. Pre-loaded resin, H-L-Ser(t-Bu)-2-Cl-Trityl resin (0.133 g, 0.1 mmol), was placed in the reaction vessel. Fmoc protected amino acids (0.4 mmol), Fmoc protected glycoamino acid (0.4 mmol) or palmitic acid (0.4 mmol) were dissolved in 5 mL of DMF and the coupling reactions were carried out by activation with HBTU (0.4 mmol) and DIPEA (0.6 mmol) in DMF.

Fmoc deprotection was carried out using 20% piperidine solution in DMF. After completion of peptide assembly, the resin was washed with DMF (3×5 mL) followed by DCM (3×5 mL) and then dried under high vacuum for 3 hours. The dried resin was then treated at room temperature for 3 hours with 10 mL of reagent K (TFA:water:phenol:thioanisole=8.5:0.5:0.5:0.5) for each 0.1 mmol resin. The crude glycopeptide product was precipitated from cold ethyl ether, purified by RP-HPLC and lyophilized to give 80-100 mg of glycopeptide as a white powder. Molecular weight of the glycopeptide was confirmed by MS and the purity was established by analytical RP-HPLC.

General Procedure for the Synthesis of Deacylated Glycosylated Oligopeptides

To solutions of Pal-KTT*KS-[OH] or Pal-KT*TKS-[OH] (0.05 mmol, respectively) in anhydrous MeOH (5 mL) was added sodium methoxide (1M) in anhydrous methanol dropwise to adjust pH to approximately 10. The reaction mixture was stirred for 1 hour at room temperature and then neutralized with acetic acid (pH~4.0). The solvent was removed in vacuo. The crude deprotected glycopeptide was purified by RP-HPLC and lyophilized to give typically 30 to 40 mg of target glycopeptide as a white powder.

General Procedure for the Synthesis of Per-Acetylated Serine Glycosylated Oligopeptides Synthesis of Pre-Loaded H-L-Ser(sugar)-2-Cl-Trityl resin: To a solution of Fmoc-Ser(sugar)-OH (0.3 mmol) in anhydrous DCM (5 mL) was added to 2-Chlorotrityl resin (0.4 g, 0.3 mmol) in a centrifuge tube. After 15 minutes, DIPEA (87 µL, 0.5 mmol) was added. The mixture was agitated on a shaker for 30 minutes followed by addition of DIPEA (120 µL, 0.75 mmol). The mixture was left on the shaker for an additional 3 hours. To end cap, methanol (0.4 mL) was added, and the mixture was agitated for an additional 30 minutes. The resin was transferred to a glass funnel fitted with a porous disc and washed with DMF (2×5 mL) followed by DCM (2×5 mL) and finally MeOH (3×5 mL). The resin was dried in vacuo overnight to yield the preloaded H-L-Ser(sugar)-2-Cl-Trityl resin for further use in Fmoc-SPPS synthesis of glycopeptides.

The serine glycosylated glycopeptides were synthesized on a CS Bio CS136XT automated synthesizer by standard Fmoc solid phase peptide synthesis methodology. The preloaded resin (H-L-Ser(sugar)-2-Cl-Trityl resin (0.1 mmol)) was placed in a reaction vessel. Fmoc protected amino acids (0.4 mmol dissolved in 5 mL of DMF) were coupled utilizing activation with HBTU (0.4 mmol) and DIPEA (0.6 mmol). N-terminating palmitic acid (0.4 mmol dissolved in 5 mL of DMF) was coupled similarly. Fmoc protecting groups were removed using 20% piperidine solution in DMF. After the peptides were assembled, the resin was washed with DMF (3×5 mL) followed by DCM (3×5 mL) and then dried under high vacuum for 3 hours. To the dried resin was added 10 mL of reagent K (TFA:water:phenol:thioanisole=8.5:0.5:0.5:0.5). The mixture was then shaken at room temperature for 3 hours. The crude glycopeptide was precipitated from cold ethyl ether, purified by RP-HPLC and lyophilized to yield 120-150 mg of the target glycopeptide as a white powder. Molecular weight of the product glycopeptide was confirmed by MS and the purity was assessed by analytical HPLC.

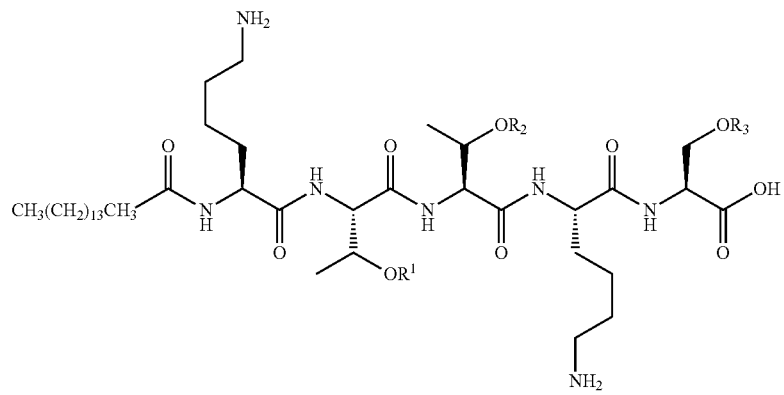

GP001-1: $R_1$ = Ac$_4$-β-Glc, $R_2$ = H, $R_3$ = H
GP003-9: $R_1$ = Ac$_7$-β-Mal, $R_2$ = H, $R_3$ = H
GP002-3: $R_1$ = H, $R_2$ = H, $R_3$ = Ac$_4$-β-Glc
GP002-7: $R_1$ = H, $R_2$ = H, $R_3$ = Ac$_4$-β-Gal
GP004-3: $R_1$ = H, $R_2$ = Ac$_7$-β-Mal, $R_3$ = H
GP004-4: $R_1$ = H, $R_2$ = H, $R_3$ = Ac$_7$-β-Mal

Exemplary Synthesis of Pal-KT(Ac$_4$-β-Glc)TKS-[OH] (GP001-1)

Glycopeptide GP001-1 (SEQ ID NO: 4) was synthesized on a CS-Bio CS136XT automated synthesizer using standard Fmoc-SPPS methodology on a H-L-Ser(t-Bu)-2-Cl-Trityl resin (133.3 mg, 0.1 mmol) and using the following general procedure. The first amino acid, Fmoc-Lys(Boc)-OH (187.4 mg, 0.4 mmol) was coupled to the preloaded resin using HBTU (128.4 mg, 0.4 mmol) and DIPEA (104.5 µL, 0.6 mmol) in DMF (5 mL). Subsequent Fmoc-amino acids and palmitic acid were coupled in the same manner. Fmoc-Thr(Ac$_4$-β-Glc)-OH (0.270 mg, 0.4 mmol) was used in the third coupling reaction. After solid-phase synthesis, the glycopeptide was cleaved from the resin with reagent K (10 mL). The resulting crude glycopeptide was purified by preparative RP-HPLC to provide Pal-KT(Ac$_4$-β-Glc)TKS-OH (SEQ ID NO: 4), GP001-1, (70 mg, 62%) as a white powder. ESI-MS: m/z: calcd for $C_{53}H_{93}N_7O_{19}$; 1132.34; found: 1133.1[M+H]$^+$. The purity was 95.6% as determined by analytical RP-HPLC.

Exemplary Synthesis of Pal-KT(β-Glc)-TKS-[OH] (GP001-2)

Glycopeptide GP001-1 (SEQ ID NO: 4) (65 mg, 0.05 mmol) was dissolved in 5 mL of anhydrous methanol and deprotected by addition of sodium methoxide in methanol as described in the general procedure above to yield 32 mg of target deacetyllated glycopeptide GP001-2 (SEQ ID NO: 12) as a white powder. ESI-MS: m/z: calcd for $C_{45}H_{85}N_7O_{15}$; 964.19; found: 965[M+H]+. The purity was 99% by analytical HPLC.

Exemplary Synthesis of Pal-KT(Ac$_7$-β-Mal)TKS-[OH] (GP003-9)

Glycopeptide GP003-9 (SEQ ID NO: 6) was synthesized on a CS-Bio CS136XT automated synthesizer using standard Fmoc-SPPS methodology on a H-L-Ser(t-Bu)-2-Cl-Trityl resin (133.3 mg, 0.1 mmol) and using the following general procedure. The first amino acid, Fmoc-Lys(Boc)-OH (187.4 mg, 0.4 mmol) was coupled to the preloaded resin using HBTU (128.4 mg, 0.4 mmol) and DIPEA (104.5 μL, 0.6 mmol) in DMF (5 mL). Subsequent Fmoc-amino acids were coupled in the same manner. Fmoc-Thr(Ac$_7$-β-Mal)-OH (0.372 mg, 0.4 mmol) was used in the third coupling reaction. After solid-phase synthesis, the glycopeptide was cleaved from the resin with reagent K (10 mL). The resultant crude glycopeptide was purified by preparative RP-HPLC to provide Pal-KT(Ac$_7$-β-Mal)TKS-OH (SEQ ID NO: 6), GP003-9 (90 mg, 63% yield) as white powder. ESI-MS: m/z: calcd for $C_{65}H_{109}N_7O_{27}$; 1420.59; found: 1420.7 [M+H]$^+$. The purity was 99.1% as determined by analytical RP-HPLC.

Exemplary Synthesis of Pal-KTTKS(Ac$_4$-β-Glc)-[OH] (GP002-3)

a) Fmoc-Ser(Ac4-β-Glc)-OH (0.3 mmol) was loaded onto 2-Chlorotrityl resin (0.4 g, 0.3 mmol) by the general procedure described above. The dried pre-loaded resin was then used without further processing in subsequent steps.

b) Glycopeptide GP002-3 (SEQ ID NO: 8) was synthesized on a CS Bio CS136XT automated synthesizer by standard Fmoc solid phase peptide synthesis methodology on pre-loaded resin prepared as described vide supra. After solid-phase synthesis, the glycopeptide was cleaved from the resin using reagent K (10 mL). The resultant crude glycopeptide was purified by preparative HPLC to provide Pal-KTTKS(Ac4-β-Glc)-OH (SEQ ID NO: 8), GP002-3 (136 mg, 40%), as white powder. ESI-MS: m/z: calcd for $C_{53}H_{93}N_7O_{19}$; 1132.34; found: 1132.5[M+H]+. The purity was 99.6% by analytical RP-HPLC.

Exemplary Synthesis of PaKTTKS(Ac$_4$-β-Gal)-[OH] (GP002-7)

a) Fmoc-Ser(Ac4-β-Gal)-OH (0.3 mmol) was loaded onto the 2-Chlorotrityl resin (0.4 g, 0.3 mmol) by general procedure described above. The dried pre-loaded resin was used without further processing in subsequent steps.

b) Glycopeptide GP002-7 (SEQ ID NO: 7) was synthesized on a CS Bio CS136XT automated synthesizer by standard Fmoc solid phase peptide synthesis methodology on pre-loaded resin prepared as described vide supra. After solid-phase synthesis, the glycopeptide was cleaved from the resin using reagent K (10 mL). The resultant crude glycopeptide was purified by preparative RP-HPLC to provide the target peptide, Pal-KTTKS(Ac4-β-Gal)-OH (SEQ ID NO: 7), GP002-7 (140 mg, 41%), as white powder. ESI-MS: m/z: calcd for $C_{53}H_{93}N_7O_{19}$; 1132.34; found: 1132.5[M+H]+. The purity was 99.6% by analytical HPLC.

Exemplary Synthesis of Pal-KTT(Ac$_7$-β-Mal)KS-[OH] (GP004-3)

Glycopeptide GP004-3 (SEQ ID NO: 9) was synthesized on a CS-Bio CS136XT automated synthesizer using standard Fmoc-SPPS methodology on a H-L-Ser(t-Bu)-2-Cl-Trityl resin (133.3 mg, 0.1 mmol) and using the following general procedure. The first amino acid, Fmoc-Lys(Boc)-OH (179.6 mg, 0.4 mmol) was coupled to the preloaded resin using HBTU (126.3 mg, 0.4 mmol) and DIPEA (104.5 μL, 0.6 mmol) in DMF (5 mL). Subsequent Fmoc-amino acids were coupled in the same manner. Fmoc-Thr(Ac$_7$-β-Mal)-OH (0.383 mg, 0.4 mmol) was used in the second coupling reaction. After solid-phase synthesis, the glycopeptide was cleaved from the resin with reagent K (10 mL). The resultant crude glycopeptide was purified by preparative RP-HPLC to provide Pal-KT(Ac$_7$-β-Mal)TKS-OH (SEQ ID NO: 9), GP004-3 (26 mg, 18% yield) as white powder. ESI-MS: m/z: calcd for $C_{65}H_{109}N_7O_{27}$; 1420.59; found: 1420.7 [M+H]$^+$. The purity was 98.5% as determined by analytical RP-HPLC.

Exemplary Synthesis of Pal-KTTKS(Ac$_7$-β-Mal)-[OH] (GP004-4)

a) Fmoc-Ser(Ac7-β-Mal)-OH (0.3 mmol) was loaded onto 2-Chlorotrityl resin (0.4 g, 0.3 mmol) by the general procedure described above. The dried pre-loaded resin was then used without further processing in subsequent steps.

b) Glycopeptide GP004-4 (SEQ ID NO: 10) was synthesized on a CS Bio CS136XT automated synthesizer by standard Fmoc solid phase peptide synthesis methodology on pre-loaded resin prepared as described vide supra. After solid-phase synthesis, the glycopeptide was cleaved from the resin using reagent K (10 mL). The resultant crude glycopeptide was purified by preparative HPLC to provide Pal-KTTKS(Ac7-β-Mal)-[OH](SEQ ID NO: 10), GP004-4 (102 mg, 24%), as white powder. ESI-MS: m/z: calcd for $C_{65}H_{109}N_7O_{27}$; 1420.59; found: 1420.7 [M+H]$^+$. The purity was 97.8% by analytical RP-HPLC.

Abbreviations:
Ac acetyl
Ac4-β-Glc 2,3,4,6-Tetra-O-acetyl-beta-D-glucopyranoside
Ac4-β-Gal 2,3,4,6-Tetra-O-acetyl-beta-D-galactopyranoside
Ac7-β-Mal 2,2',3,3',4',6,6'-Hepta-O-beta-D-maltopyranoside
Cel D-cellobiose
Cl chlorine
Gal D-galactose
GalNAc N-acetyl-D-galactosamine
Glc D-glucose
GlcNAc N-acetyl-D-glucosamine
DCM Dichloromethane
DIPEA N,N-diisopropylethylamine
DMF Dimethylformamide
Fuc L-fucose
HBTU N,N,N',N'-Tetramethyl-O-(1H-benzotriazol-1-yl) uronium hexafluorophosphate
Lac D-lactose
Mal D-maltose Man D-mannose
MeOH Methanol
Pal palmitoyl
Rha L-rhamnose
t-Bu tert-butyl
TFA Trifluoroacetic acid
Xyl D-xylose Mass Spectrometry Mass spectra of the peptides were obtained via injection of a sample (2-5 µL) of the peptides dissolved in water onto an LC-MS system (HPLC: Waters Alliance 2795). Mobile phases consisted of water:Formic acid (100:0.1) and acetonitrile:formic acid (100:0.1) for mobile phase A and B respectively. The flow rate was set to 0.2 mL/min with a composition of 50:50 (mobile phase A:mobile phase B). The mass spectrometer (Mass Spec: Waters Micromass ZQ) was set to scan from 100-1800 amu in 1 second for both positive and negative modes over a 2.0 minute run time. Mass spectra were extracted from the TIC chromatograms.

ECM ELISA Assay

KMST-6 cells (Japan Health Sciences Foundation, JCRB0433) were seeded at 7,000 cells/ml in 12-well tissue culture treated plates (Falcon, 353043) in complete media. The complete media consisted of the following: MEM/EBSS (Hyclone, SH30024.01), 10% Heat-Inactivated FBS (Gibco, 10082-147), 1% L-Glutamine (Hyclone, SH30031.01), 1% Nucleosides (800 mg/L Adenosine, 850 mg/L Guanidine, 730 mg/L Cytidine, 730 mg/L Uridine and 240 mg/L Thymidine), 1% Penicillin/Streptomycin (HyClone, SV30010), 1% Sodium Pyruvate (HyClone, SH30239.01), 1% Non-Essential Amino Acids (Hyclone, SH30238.01) and 0.04% Gentamicin (Gibco, 15710-064). Cells were grown for 2 days prior to treatments. The media was aspirated and cells were washed with 1×PBS (Fisher, SH30256.01) and treated with 5 µM (1 mL/well) glycopeptides, reference (Pal-KTTKS, CPC Scientific, 822197), and control (DMSO, Fisher, BP231-100) in serum-free media supplemented with 50 µg/mL Sodium Ascorbate (Sigma, A4034) and 80 µg/mL β-Aminopropionate Fumarate (Sigma, A3134). The treated cells were incubated at 37° C. and 5% $CO_2$ for 48 and 72 hours. At each timepoint, media from each treatment was collected and centrifuged at 1500 RPM for 15 minutes at 4° C. The supernatant was collected and stored at −80° C. for extracellular matrix protein quantification. The following kits were used for quantification of ECM proteins: Fibronectin (Takara, MK115) and Elastin (Uscn Life Science Inc., E91337Hu). The cells were harvest and lysed with 250 µL Lysis Buffer (20 mM Tris-HCl (Sigma, T1503), 137 mM NaCl (Sigma, S9888), 2 mM EDTA (Fisher, BP118), 1% IGEPAL (Sigma, 18896), 10% Glycerol (Sigma, G5516), 100 µM PMSF (Fisher, 36978) and 10 µg/mL Leupeptin (Sigma-Aldrich, L2884). They were placed on a container of ice on a plate shaker (Lab-Line Instruments, 3595) for 30 minutes. The lysate was centrifuged at 10,000 g for 5 minutes at 4° C. The supernatant was collected and used for protein quantification (BioRad, 500-0112).

Cell Morphology

KMST-6 cells (Japan Health Sciences Foundation, JCRB0433) were seeded at 7,000 cells/ml in 12-well tissue culture treated plates (Falcon, 353043) in complete media. The complete media consists of the following: MEM/EBSS (Hyclone, SH30024.01), 10% Heat-Inactivated FBS (Gibco, 10082-147), 1% L-Glutamine (Hyclone, SH30031.01), 1% Nucleosides (800 mg/L Adenosine, 850 mg/L Guanidine, 730 mg/L Cytidine, 730 mg/L Uridine and 240 mg/L Thymidine), 1% Penicillin/Streptomycin (HyClone, SV30010), 1% Sodium Pyruvate (HyClone, SH30239.01), 1% Non-Essential Amino Acids (Hyclone, SH30238.01) and 0.04% Gentamicin (Gibco, 15710-064). Cells were grown for 2 days prior to treatments. The media was aspirated and cells were washed with 1×PBS (Fisher, SH30256.01) and treated with 5 µM glycopeptides (GP001-1, GP002-3, GP002-7, GP003-9, GP004-3 and GP004-4), reference (Pal-KTTKS, CPC Scientific, 822197), and control (DMSO, Fisher, BP231-100) in serum-free media supplemented with 50 µg/mL Sodium Ascorbate (Sigma, A4034) and 80 µg/mL β-Aminopropionate Fumarate (Sigma, A3134). The treated cells were incubated at 37° C. and 5% $CO_2$ for 48 and 72 hours. At each time point, images were taken with an Olympus Opti-Tech Scientific Microscope (Lumenera, Infinity 2 camera at 10× magnification) and changes in cell size and morphology were recorded.

Cell Viability MTT Assay

KMST-6 cells (Japan Health Sciences Foundation, JCRB0433) were seeded at 7,000 cells/ml in complete media. The complete media consists of the following: MEM/EBSS (Hyclone, SH30024.01), 10% Heat-Inactivated FBS (Gibco, 10082-147), 1% L-Glutamine (Hyclone, SH30031.01), 1% Nucleosides (800 mg/L Adenosine, 850 mg/L Guanidine, 730 mg/L Cytidine, 730 mg/L Uridine and 240 mg/L Thymidine), 1% Penicillin/Streptomycin (HyClone, SV30010), 1% Sodium Pyruvate (HyClone, SH30239.01), 1% Non-Essential Amino Acids (Hyclone, SH30238.01) and 0.04% Gentamicin (Gibco, 15710-064). Cells were grown for 2 days prior to treatments. The media was aspirated and cells were washed with 1×PBS (Fisher, SH30256.01) and treated with 5 µM glycopeptides (GP001-1, GP002-3, GP002-7, GP003-9, GP004-3 and GP004-4), reference (Pal-KTTKS, CPC Scientific, 822197), and control (DMSO, Fisher, BP231-100) in serum-free media supplemented with 50 µg/mL Sodium Ascorbate (Sigma, A4034) and 80 µg/mL β-Aminopropionate Fumarate (Sigma, A3134). The treated cells were incubated at 37° C. and 5% $CO_2$ for 48 and 72 hours. At each timepoint, the MTT Assay was performed by adding 15 µL of the Dye Solution (Promega, G4102) to all wells. Cells were allowed to incubate for 2-4 hours. During this time, living cells convert the MTT tetrazolium component of the Dye Solution into a formazan product. The Solubilization/Stop Solution (Promega, G4101) was then added to the culture wells to solubilize the formazan product. The absorbance was measured with a microplate reader (Molecular Devices, SpectraMax M2e) at 570 nm. We have defined toxicity as the cell viability that is less than 50% when compared to control.

Total Collagen Assay

KMST-6 cells (Japan Health Sciences Foundation, JCRB0433) were seeded at 7,000 cells/mL in 60 mm tissue culture treated plates (Falcon, 353002) in complete media. The complete media consisted of the following: MEM/EBSS (Hyclone, SH30024.01), 10% Heat-Inactivated FBS (Gibco, 10082-147), 1% L-Glutamine (Hyclone, SH30031.01), 1% Nucleosides (800 mg/L Adenosine, 850 mg/L Guanidine, 730 mg/L Cytidine, 730 mg/L Uridine and 240 mg/L Thymidine), 1% Penicillin/Streptomycin (HyClone, SV30010), 1% Sodium Pyruvate (HyClone, SH30239.01), 1% Non-Essential Amino Acids (Hyclone, SH30238.01) and 0.04% Gentamicin (Gibco, 15710-064). Cells were grown for 2 days prior to treatments. The cells were washed with 1×PBS (Fisher, SH30256.01) and treated with 5 µM glycopeptides (GP003-9, GP004-3, GP004-4), reference (Pal-KTTKS, CPC Scientific, 822197), and control (DMSO, Fisher, BP231-100) in serum-free media supplemented with 50 g/mL Sodium Ascorbate (Sigma, A4034) and 80 µg/mL β-Aminopropionate Fumarate (Sigma, A3134). The treated cells were incubated at 37° C. and 5% $CO_2$ for 48 and 72 hours. At each timepoint, media from each treatment was collected and centrifuged at 1500 RPM for 15 minutes at 4° C. The supernatant was collected and stored at −80° C. for extracellular matrix protein quantification. The following kit was used for quantification of total collagen: Sirius Red Collagen Detection Kit (Chondrex Inc., 9062). The cells were harvested and lysed with Lysis Buffer (20 mM Tris-HCl (Sigma, T1503), 137 mM NaCl (Sigma, S9888), 2 mM EDTA (Fisher, BP118), 1% IGEPAL (Sigma, 18896), 10% Glycerol (Sigma, G5516), 100 µM PMSF (Fisher, 36978) and 10 µg/mL Leupeptin (Sigma, L2884)). They were placed on a container of ice on an orbital shaker (VWR, 89032-088) for 30 minutes. The cell lysate was centrifuged at 10,000 g for 5 minutes at 4° C. The supernatant was collected and used for protein quantification (BioRad, 500-0112).

3D Human In Vitro Skin Model

MatTek's EpiDermFT™ 3D human in vitro skin model was produced by MatTek Corporation (Ashland, Mass., USA). The 3D skin model is comprised of normal human epidermal keratinocytes (NHEK) and normal human dermal fibroblasts (NHDF) derived from neonatal-foreskin tissue and adult skin, respectively. The histology of the tissue revealed 8-12 cell layers plus stratum corneum including basal, spinous and granular layers. The tissues were grown at air-liquid interface in Costar Snapwell™ single well tissue culture plate inserts with 0.4 µm pore size, 1.2 cm in diameter and 1.0 $cm^2$ surface area. For tissue maintenance, serum-free EFT-400-ASY media was used containing Dulbecco's Modified Eagle's Medium (DMEM), epidermal growth factor, insulin, hydrocortisone, 5 µg/mL gentamicin, 0.2 µg/ml amphotericin B and phenol red.

Elastin Assessment

Tissues were rinsed twice with 1% PBS and treated with 5 µM GP003-9, reference (Pal-KTTKS, CPC Scientific, 822197), and control (DMSO, Fisher, BP231-100). At 72 hours post treatment, supernatants were isolated and kept at −80° C. for elastin ELISA analysis (Cedarlane, SE9133Hu). ELISA was performed according to the manufacturer's protocol using 1:50 sample dilution.

For total protein quantification, tissues were rinsed with 1% PBS and cold Tissue Protein Extraction Reagent (Pierce, 78510) was added. Tissues were homogenized for approximately 1 minute using a hand-held pellet pestle. All samples were centrifuged at 16,000 g for 10 minutes at 4° C. Following centrifugation, supernatants were collected and the protein concentration was determined using the BCA Protein Assay Kit (Pierce, 23227).

Histological Processing

Tissues were rinsed twice with 1% PBS and treated with 5 µM GP003-9, reference (Pal-KTTKS, CPC Scientific, 822197), and control (DMSO, Fisher, BP231-100). At 72 hours post treatment, the tissue was fixed in 10% neutral buffered formalin overnight and transferred to 1% PBS the next day. Tissues were then bisected (to provide a cross-section), dehydrated in a series of graded ethanol and embedded in paraffin. Five micron sections were prepared and stained with hematoxylin & eosin for use in histological observations.

Statistical Analysis

One-way Anova statistical technique was used to compare means of three or more samples. Bonferroni multiple comparison tests allowed a comparison of the difference between glycopeptide's treatment with control or reference. Statistical significance was derived by setting p value at $p<0.05$. (Data analysis was obtained using GraphPad Prism 6, a scientific software, which enabled the performance of basic statistical tests, data organization and scientific graphing.)

The following examples describe some exemplary modes of making and practicing certain compositions and methods that are described herein. It should be understood that these examples are for illustrative purposes only and are not meant to limit the scope of the compositions and methods described herein.

Example 1

Four batches of modified peptides were made and chemical identity was confirmed by HPLC and Mass Spectrometry as described previously. In total 44 different glycopeptides were made and are shown in Tables 1A and 1B.

TABLE 1A

Synthesized Glycopeptides

| Group# | GP001 | GP002 |
|---|---|---|
| Cmpd -1 | Pal-KT($Ac_4$-β-Glc)TKS-OH (SEQ ID NO: 4) | Pal-KTTKS($Ac_3$-α-GalNAc)-OH (SEQ ID NO: 25) |
| Cmpd -2 | Pal-KT(β-Glc)TKS-OH (SEQ ID NO: 12) | Pal-KTTKS(α-GalNAc)-OH (SEQ ID NO: 26) |
| Cmpd -3 | Pal-KT($Ac_3$-α-GalNAc)TKS-OH (SEQ ID NO: 13) | Pal-KTTKS($Ac_4$-β-Glc)-OH (SEQ ID NO: 8) |
| Cmpd -4 | Pal-KT(α-GalNAc)TKS-OH (SEQ ID NO: 14) | Pal-KTTKS(β-Glc)-OH (SEQ ID NO: 27) |
| Cmpd -5 | Pal-KT($Ac_3$-β-GlcNAc)TKS-OH (SEQ ID NO: 15) | Pal-KTTKS($Ac_3$-β-GlcNAc)-OH (SEQ ID NO: 28) |
| Cmpd -6 | Pal-KT(β-GlcNAc)TKS-OH (SEQ ID NO:16) | Pal-KTTKS(β-GlcNAc)-OH (SEQ ID NO: 29) |
| Cmpd -7 | Pal-KTT($Ac_4$-β-Glc)KS-OH (SEQ ID NO: 17) | Pal-KTTKS($Ac_4$-β-Gal)-OH (SEQ ID NO: 7) |
| Cmpd -8 | Pal-KTT(β-Glc)KS-OH (SEQ ID NO: 18) | Pal-KTTKS(β-Gal)-OH (SEQ ID NO: 30) |

TABLE 1A-continued

Synthesized Glycopeptides

| Group# | GP001 | GP002 |
|---|---|---|
| Cmpd -9 | Pal-KTT(Ac$_3$-α-GalNAc)KS-OH (SEQ ID NO: 19) | |
| Cmpd -10 | Pal-KTT(α-GalNAc)KS-OH (SEQ ID NO: 20) | |
| Cmpd -11 | Pal-KTT(Ac$_3$-β-GlcNAc)KS-OH (SEQ ID NO: 21) | |
| Cmpd -12 | Pal-KTT(β-GlcNAc)KS-OH (SEQ ID NO: 22) | |
| Cmpd -13 | Pal-KT(Ac$_3$-α-GalNAc)-T(Ac$_3$-α-GalNAc)KS-OH (SEQ ID NO: 23) | |
| Cmpd -14 | Pal-KT(α-GalNAc)-T(α-GalNAc)KS-OH (SEQ ID NO: 24) | |

TABLE 1B

Synthesized Glycopeptides

| Group# | GP003 | GP004 |
|---|---|---|
| Cmpd -1 | Pal-KT(Ac$_4$-α-Man)TKS-OH (SEQ ID NO: 5) | Pal-KT(Ac$_4$-β-Gal)TKS-OH (SEQ ID NO: 39) |
| Cmpd -2 | Pal-KT(α-Man)TKS-OH (SEQ ID NO: 31) | Pal-KTT(Ac$_4$-β-Gal)KS-OH (SEQ ID NO:40) |
| Cmpd -3 | Pal-KS(Ac$_4$-β-Glc)TKS-OH (SEQ ID NO: 32) | Pal-KTT(Ac$_7$-β-Mal)KS-OH (SEQ ID NO: 9) |
| Cmpd -4 | Pal-KS(β-Glc)TKS-OH (SEQ ID NO: 33) | Pal-KTTKS(Ac$_7$-β-Mal)-OH (SEQ ID NO: 10) |
| Cmpd -5 | Pal-KN(Ac$_4$-β-Glc)TKS-OH (SEQ ID NO: 34) | Pal-KT(Ac$_7$-β-Lac)TKS-OH (SEQ ID NO: 41) |
| Cmpd -6 | Pal-KN(β-Glc)TKS-OH (SEQ ID NO: 35) | Pal-KTTKS(Ac$_7$-β-Lac)-OH (SEQ ID NO: 42) |
| Cmpd -7 | Pal-N(Ac$_4$-β-Glc)KTTKS-OH (SEQ ID NO: 36) | Pal-KT(Ac$_3$-α-Rha)TKS-OH (SEQ ID NO: 43) |
| Cmpd -8 | Pal-N(β-Glc)KTTKS-OH (SEQ ID NO: 37) | Pal-KTTKS(Ac$_3$-α-Rha)-OH (SEQ ID NO: 44) |
| Cmpd -9 | Pal-KT(Ac$_7$-β-Mal)TKS-OH (SEQ ID NO: 6) | Pal-KT(Ac$_7$-β-Cel)TKS-OH (SEQ ID NO: 45) |
| Cmpd -10 | Dal-KT(β-Mal)TKS-OH (SEQ ID NO: 38) | Pal-KTTKS(Ac$_7$-β-Cel)-OH (SEQ ID NO: 46) |
| Cmpd -11 | | Pal-KTTKS(Ac$_3$-β-Xyl)-OH (SEQ ID NO: 47) |
| Cmpd -12 | | Pal-KTTKS(Ac$_3$-β-Fuc)-OH (SEQ ID NO: 48) |

To determine effects on extracellular matrix protein secretion, 5 μM of individual glycopeptides were incubated with Human Dermal Fibroblasts (KMST-6). The control sample cells were treated with DMSO (Fisher, BP231-100). As described previously, supernatant was collected from treated cells (at two time-points, 48 and 72 hours of treatment) and stored at −80° C. for subsequent extracellular matrix protein quantification using ELISA kits (Fibronectin (Takara, MK115), Elastin (Uscn Life Science Inc., E91337Hu). For the determination of total cellular protein, treated cells were harvested and lysed. The lysate was centrifuged, the supernatant was collected and then used for protein quantification (BioRad, 500-0112). ELISA plates were read on the plate reader (Molecular Devices) at absorbance of 450 nm and SoftMax Pro software was used to compute the μg/ml values of protein of interest derived from the generated 4-parameter fit standard curve. Each μg/ml of protein secreted was normalized to total protein per well. The data was analysed by averaging out normalized values from at least three independent experiments and presenting them as a % compared to control treatment set at 100% (Table 2-5). Statistical significance was performed using One-way ANOVA (p<0.05) where "*" represents statistical significance when compared to control and "#" represents statistical significance when compared to reference.

Figure 1B:
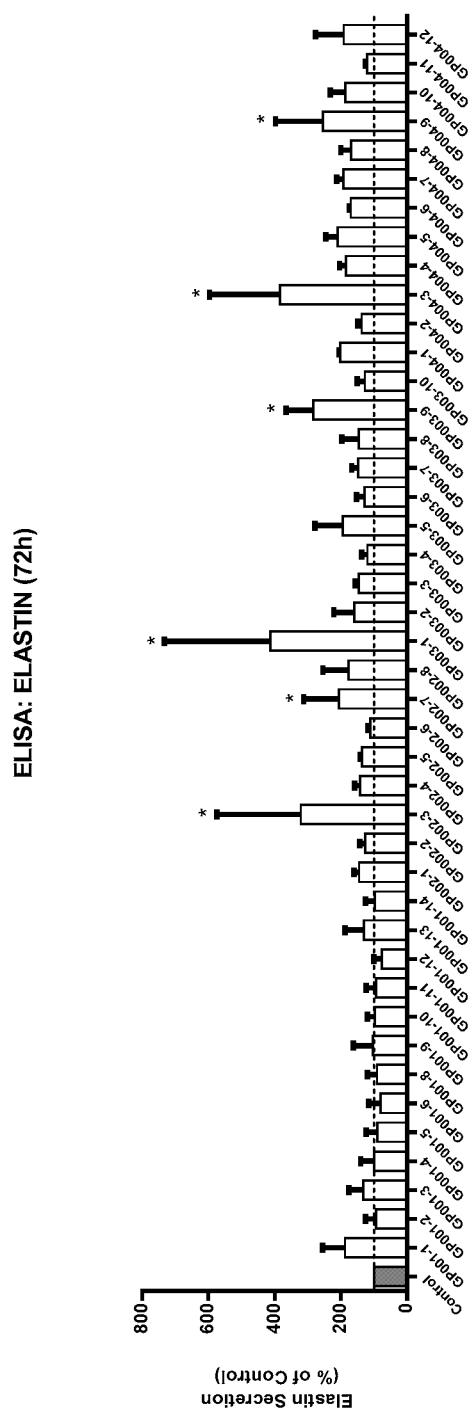
Figure 2A:
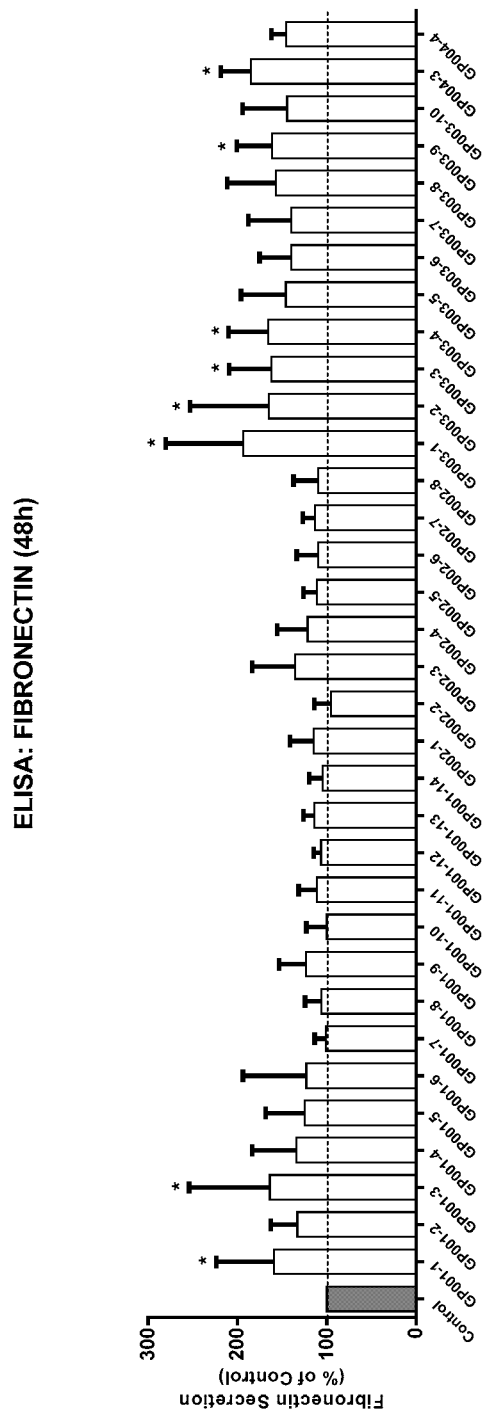
FIG. 2 is a graph showing the comparison of the efficacy of exemplary glycopeptides on fibronectin secretion as % of control at 48 hours (A) and 72 hours (B) post-treatment of human dermal fibroblasts.
Figure 2B:
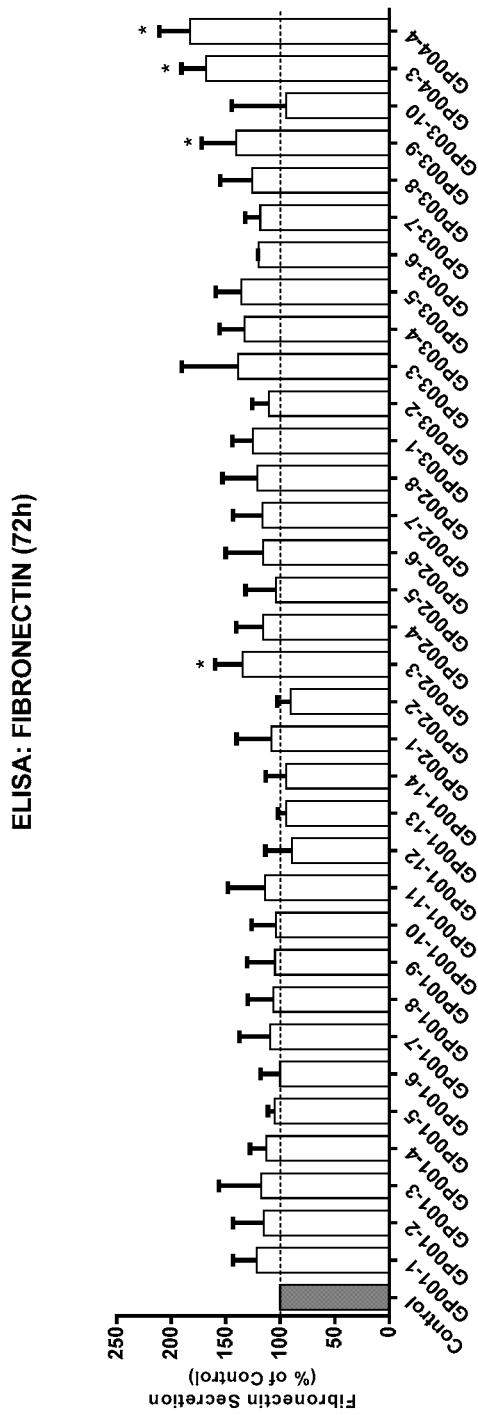

The following tables show the efficacy of all 44 glycopeptides on elastin secretion (Table 2 and Table 3 at 48 and 72 hours, respectively), and on fibronectin secretion (Table 4 and Table 5 at 48 and 72 hours, respectively) post-treatment of human dermal fibroblasts. Graphic depiction of these results are shown in FIGS. 1A and 1B (elastin secretion at 48 and 72 hours, respectively) and in FIGS. 2A and 2B (fibronectin secretion at 48 and 72 hours, respectively). From these results it can be seen that glycosylated peptides treated fibroblast cells exhibited an increased ECM secretion (elastin and fibronectin) over control treated fibroblast cells.

TABLE 2

Elastin Secretion at 48 hours

| Compound # | GP001 | GP002 | GP003 | GP004 |
|---|---|---|---|---|
| Control | | 100% | | |
| 1 | 205.3 | 144.8 | 464.1* | 215.3 |
| 2 | 102.8 | 143.8 | 121.0 | 186.5 |
| 3 | 123.3 | 460.4* | 177.1 | 226.1 |
| 4 | 104.5 | 145.0 | 136.8 | 190.0 |
| 5 | 81.67 | 159.3 | 211.4 | 195.3 |
| 6 | 91.00 | 150.7 | 170.3 | 218.6 |
| 7 | | 198.3 | 105.0 | 241.0 |
| 8 | 94.25 | 103.8 | 111.3 | 166.8 |
| 9 | 103.7 | | 255.8* | 199.3 |
| 10 | 103.0 | | 149.5 | 211.3 |
| 11 | 114.3 | | | 178.8 |
| 12 | 73.00 | | | 151.4 |
| 13 | 123.8 | | | |
| 14 | 88.00 | | | |

TABLE 3

Elastin Secretion at 72 hours

| Compound # | GP001 | GP002 | GP003 | GP004 |
|---|---|---|---|---|
| Control | | 100% | | |
| 1 | 188.0 | 145.5 | 413.6* | 202.0 |
| 2 | 94.50 | 127.0 | 160.4 | 138.3 |
| 3 | 132.5 | 321.6* | 146.8 | 384.7* |
| 4 | 100.0 | 142.0 | 120.8 | 185.5 |
| 5 | 90.00 | 137.3 | 194.2 | 209.5 |
| 6 | 81.50 | 111.0 | 128.8 | 170.0 |
| 7 | | 207.1* | 148.2 | 193.0 |
| 8 | 91.25 | 177.8 | 146.5 | 169.3 |
| 9 | 104.3 | | 283.6* | 254.6* |
| 10 | 98.67 | | 127.6 | 187.0 |
| 11 | 94.75 | | | 121.3 |
| 12 | 76.75 | | | 191.8 |
| 13 | 131.3 | | | |
| 14 | 98.25 | | | |

TABLE 4

Fibronectin secretion at 48 hours

| Compound # | GP001 | GP002 | GP003 | GP004 |
|---|---|---|---|---|
| Control | | 100% | | |
| 1 | 159.3* | 114.7 | 193.7* | |
| 2 | 133.0 | 95.7 | 165.0* | |

TABLE 4-continued

Fibronectin secretion at 48 hours

| Compound # | GP001 | GP002 | GP003 | GP004 |
|---|---|---|---|---|
| 3 | 163.8* | 135.5 | 162.0* | 185.0* |
| 4 | 134.2 | 121.5 | 165.8* | 145.7 |
| 5 | 125.0 | 111.3 | 146.0 | |
| 6 | 123.2 | 109.7 | 140.2 | |
| 7 | 101.3 | 113.7 | 139.8 | |
| 8 | 106.4 | 110.0 | 157.2 | |
| 9 | 123.4 | | 161.4* | |
| 10 | 100.2 | | 144.5 | |
| 11 | 111.2 | | | |
| 12 | 106.5 | | | |
| 13 | 114.0 | | | |
| 14 | 104.8 | | | |

TABLE 5

Fibronectin Secretion at 72 hours

| Compound # | GP001 | GP002 | GP003 | GP004 |
|---|---|---|---|---|
| Control | | 100% | | |
| 1 | 121.5 | 108.0 | 125.3 | |
| 2 | 115.4 | 90.60 | 110.3 | |
| 3 | 117.4 | 134.5* | 138.8 | 168.3* |
| 4 | 112.5 | 116.0 | 132.5 | 182.7* |
| 5 | 105.0 | 104.2 | 136.0 | |
| 6 | 100.0 | 115.8 | 119.7 | |
| 7 | 109.4 | 116.1 | 118.5 | |
| 8 | 106.2 | 121.0 | 126.0 | |
| 9 | 104.8 | | 140.4* | |
| 10 | 104.0 | | 94.70 | |
| 11 | 113.8 | | | |
| 12 | 89.25 | | | |
| 13 | 94.50 | | | |
| 14 | 94.75 | | | |

From this initial screen, 6 glycopeptides: GP001-1 (Pal-KT(Ac$_4$-Glc)TKS-OH), GP002-3 ((Pal-KTTKS(Ac$_4$-Glc)-OH), GP002-7 (Pal-KTTKS(Ac$_4$-Gal)-OH), GP003-9 (Pal-KT(Ac$_7$-β-Mal)TKS-OH), GP004-3 (Pal-KTT(Ac$_7$-β-Mal)KS-OH) and GP004-4 (Pal-KTTKS(Ac$_7$-β-Mal)-OH) (SEQ ID Nos: 4, 8, 7, 6, 9 and 10, respectively), that showed increased efficacy (ECM secretion) were identified for further development.

Figure 3A:
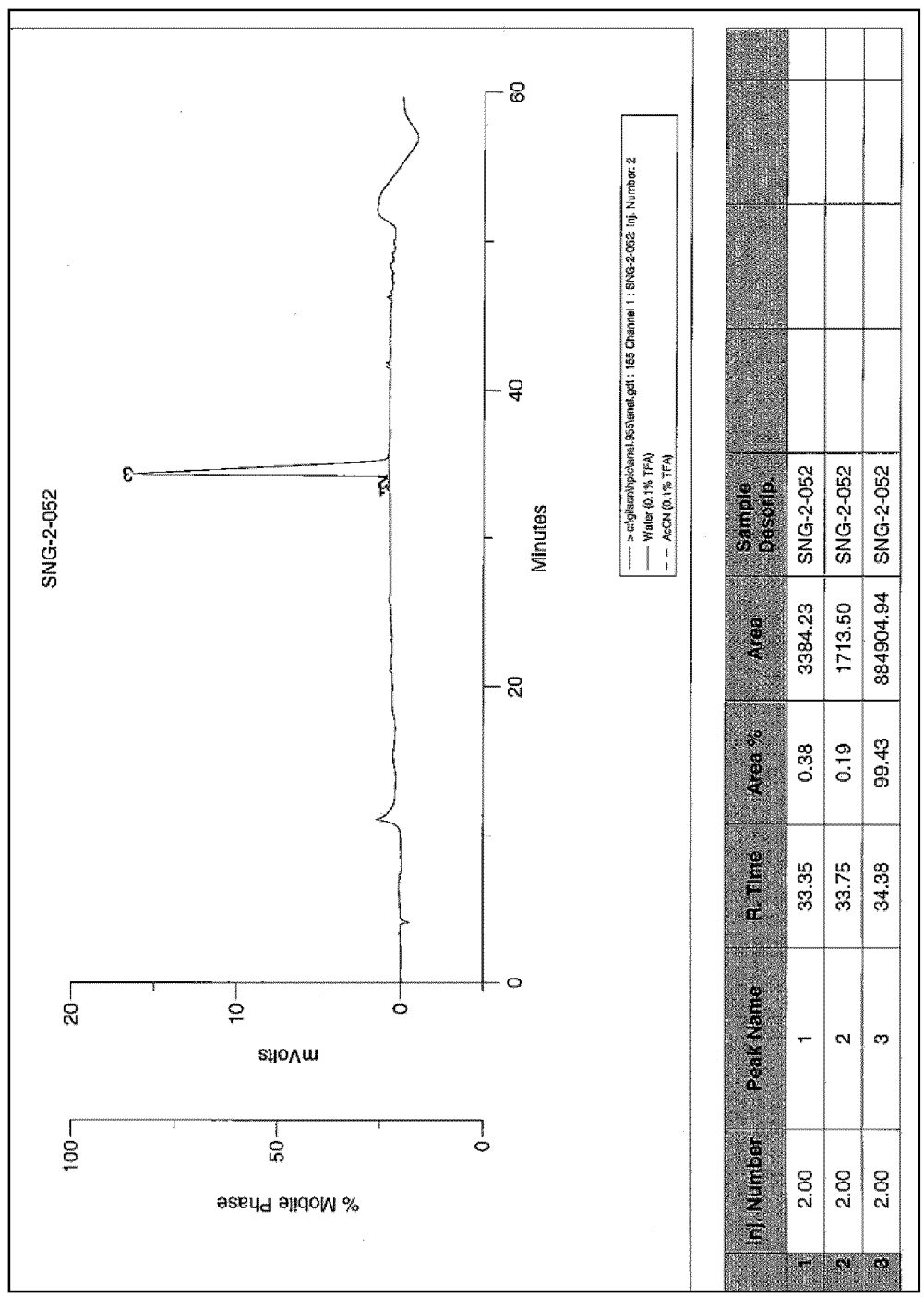
FIG. 3A is a graph that shows the HPLC profile for an exemplary compound GP001-1 (SEQ ID NO: 4).
Figure 3B:
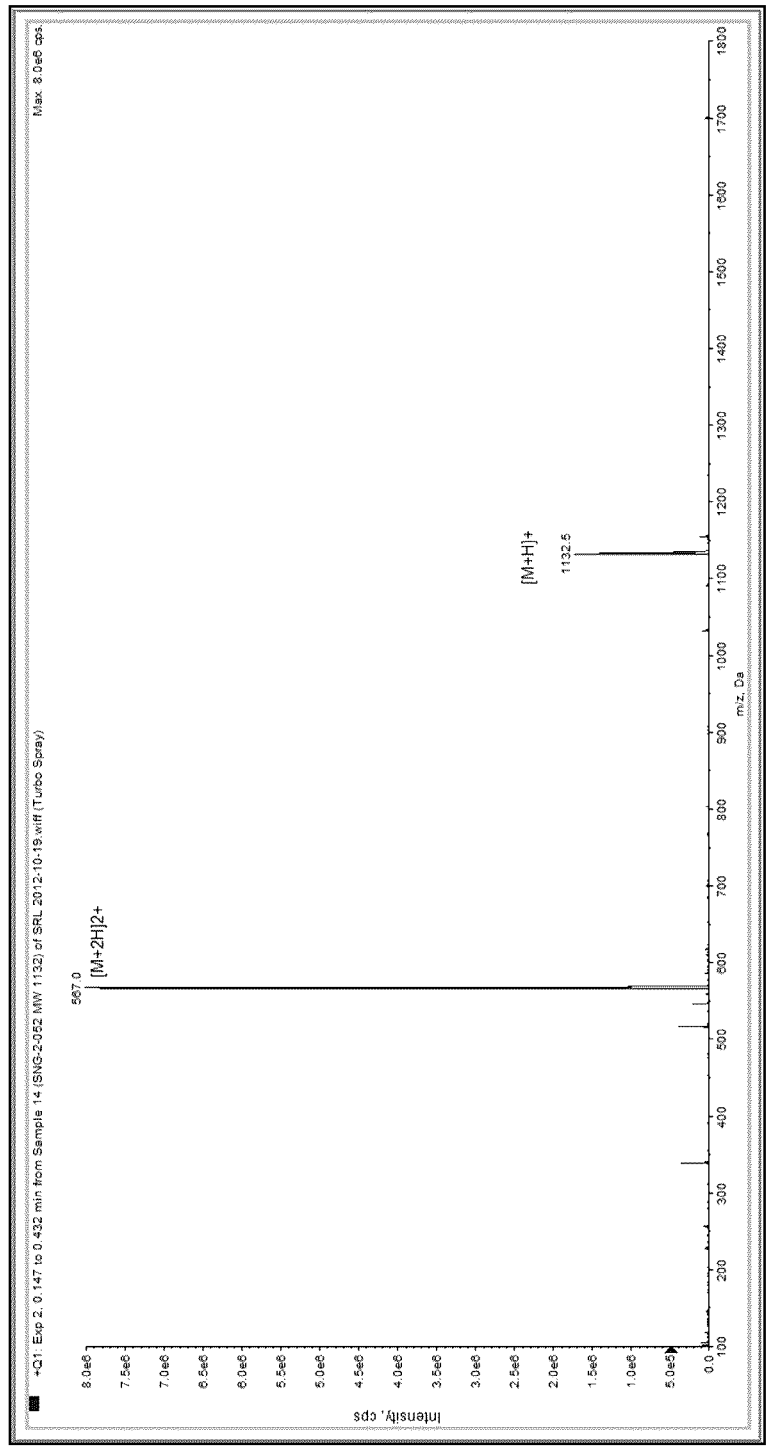
FIG. 3B is a graph that shows the Mass Spectrometry for an exemplary compound GP001-1 (SEQ ID NO: 4).

GP001-1 (Pal-KT(Ac$_4$-β-Glc)TKS-OH) (SEQ ID NO: 4)-Material: Glycopeptide (β-Glc peptide PerAc); Molecular weight: 1132; Appearance: white lyophilized solid; Purity (HPLC) >95% (FIG. 3A); Mass Spectrometry (ESI POS): conforms [M+H]$^+$=1132.5 and [M+2H]$^+$=567 (FIG. 3B).

Figure 4A:
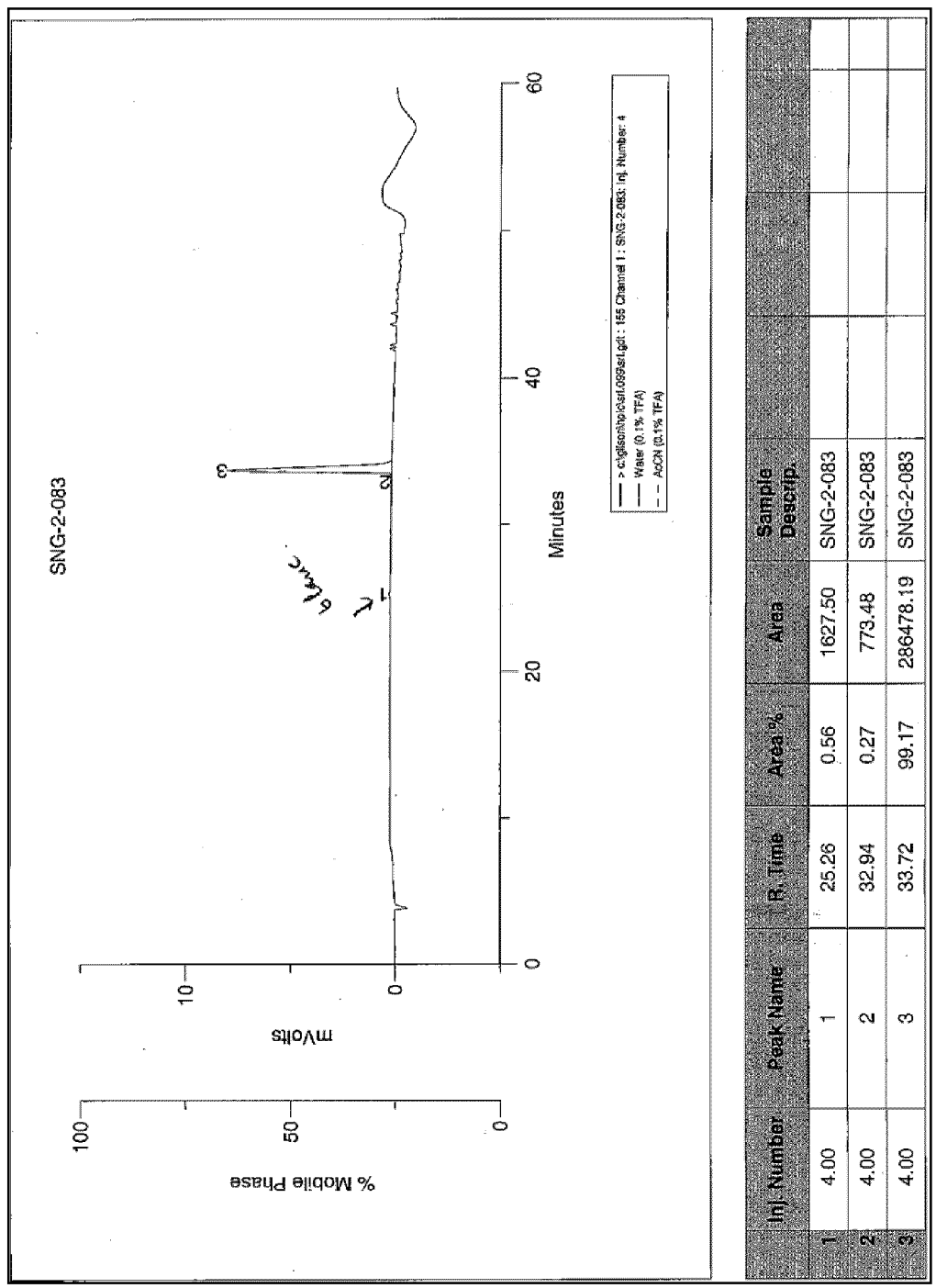
FIG. 4A is a graph that shows the HPLC profile for an exemplary compound GP002-3 (SEQ ID NO: 8).
Figure 4B:
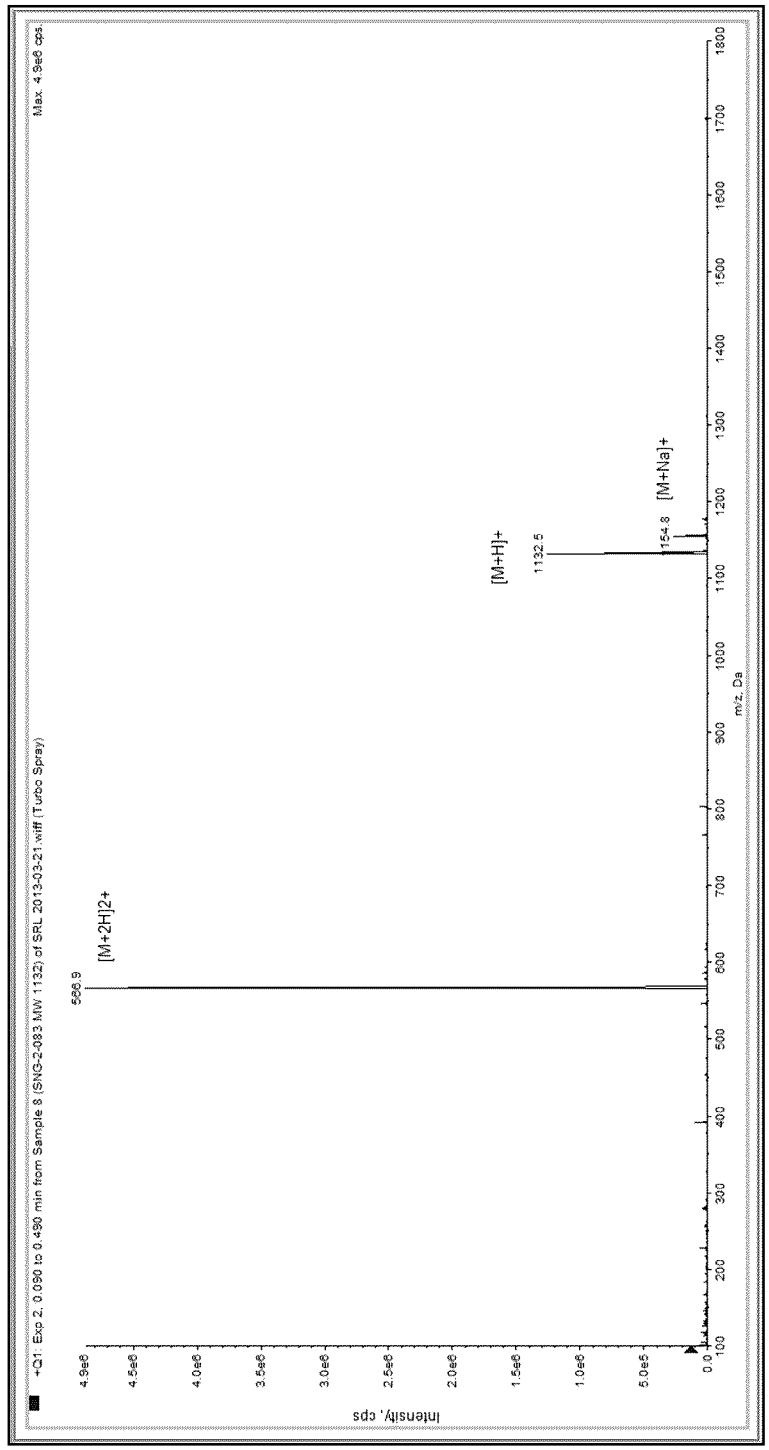
FIG. 4B is a graph that shows the Mass Spectrometry for an exemplary compound GP002-3 (SEQ ID NO: 8).

GP002-3 ((Pal-KTTKS(Ac$_4$-β-Glc)-OH) (SEQ ID NO: 8)—Material: Glycopeptide (β-Glc peptide PerAc); Molecular weight: 1132; Appearance: white lyophilized solid; Purity (HPLC) >99.6% (FIG. 4A); Mass Spectrometry (ESI POS): conforms [M+H]=1132.5 (FIG. 4B).

Figure 5A:
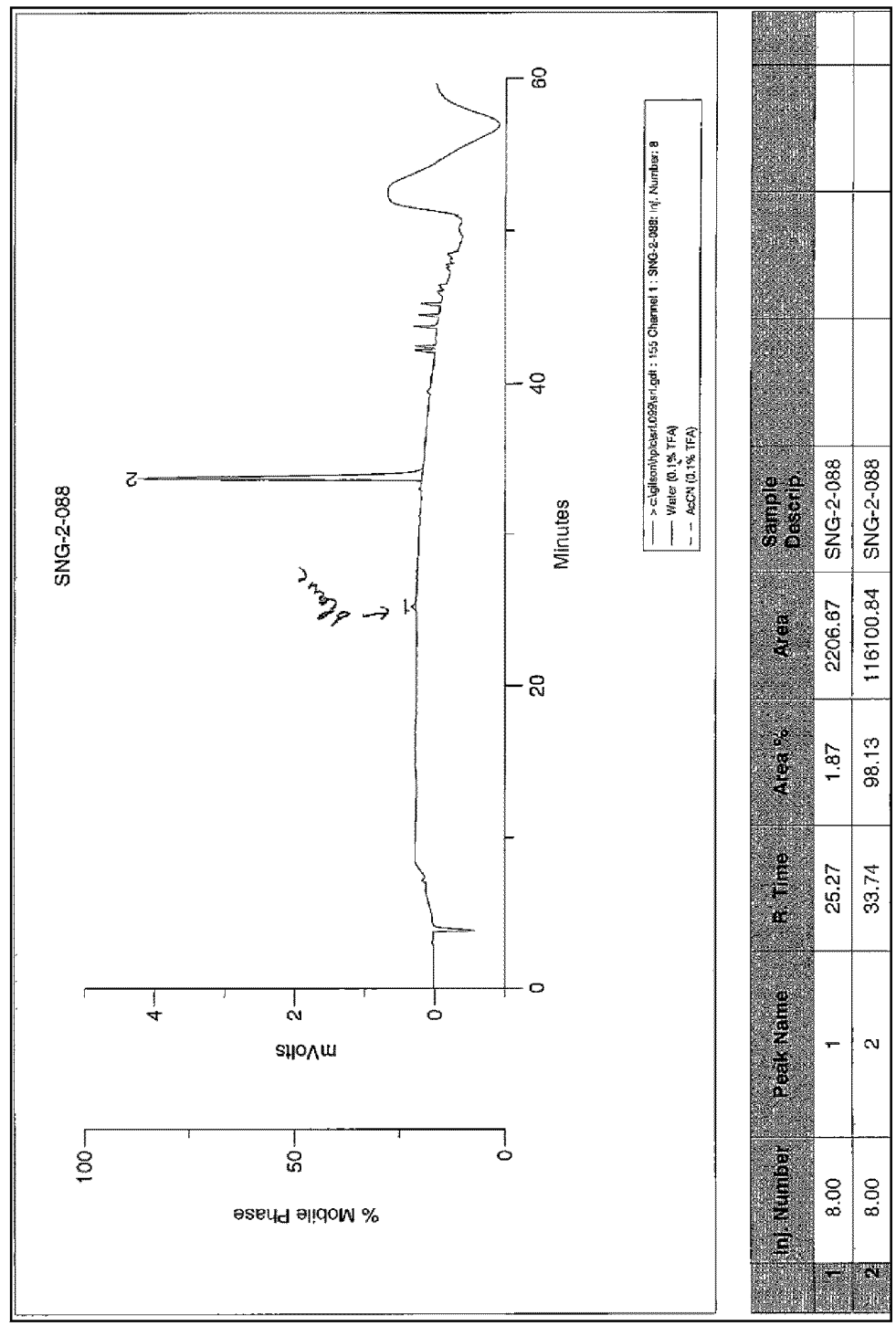
FIG. 5A is a graph that shows the HPLC profile for GP002-7 (SEQ ID NO: 7).
Figure 5B:
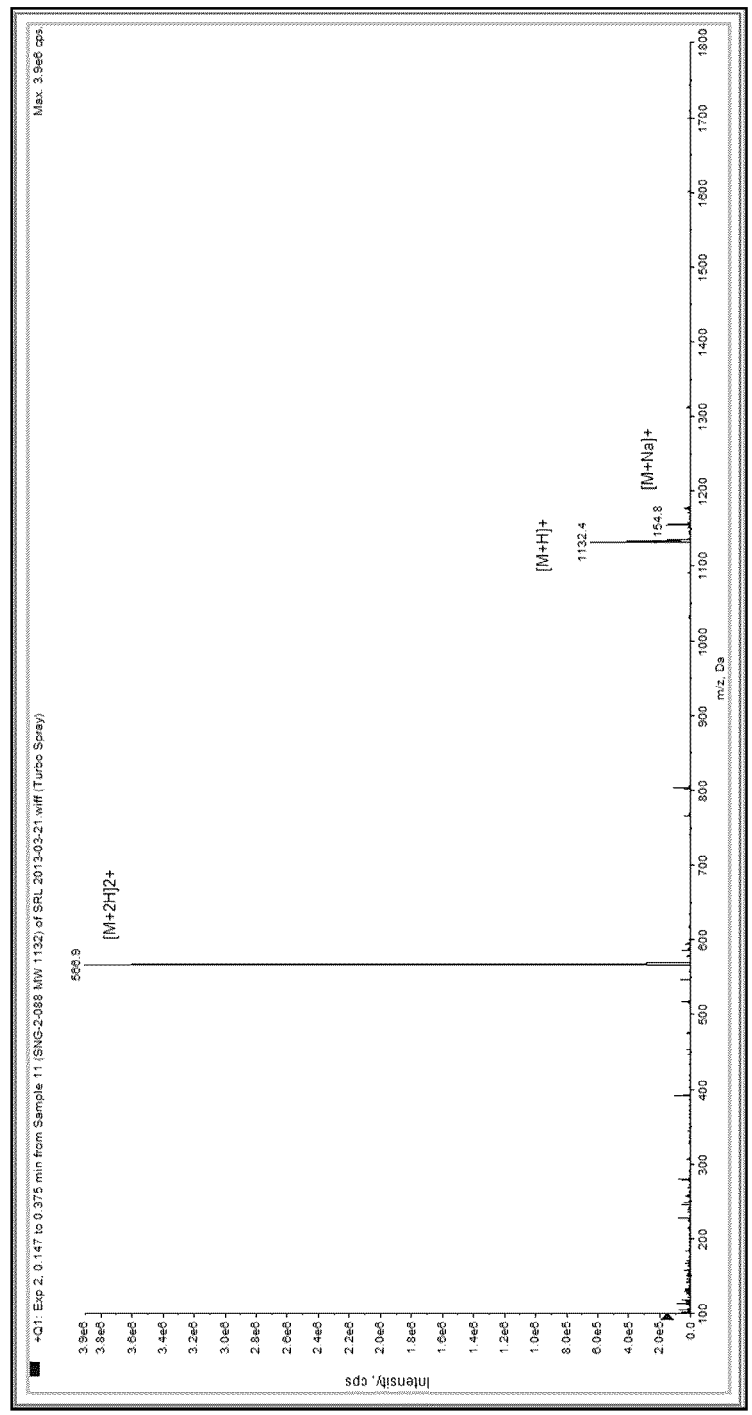
FIG. 5B is a graph that shows the Mass Spectrometry for GP002-7 (SEQ ID NO: 7).

GP002-7 (Pal-KTTKS(Ac$_4$—O-Gal)-OH) (SEQ ID NO: 7)—Material: Glycopeptide (β-Glc peptide PerAc); Molecular weight: 1132; Appearance: white lyophilized solid; Purity (HPLC) >100% (FIG. 5A); Mass Spectrometry (ESI POS): conforms [M+H]=1132.4 (FIG. 5B).

Figure 6A:
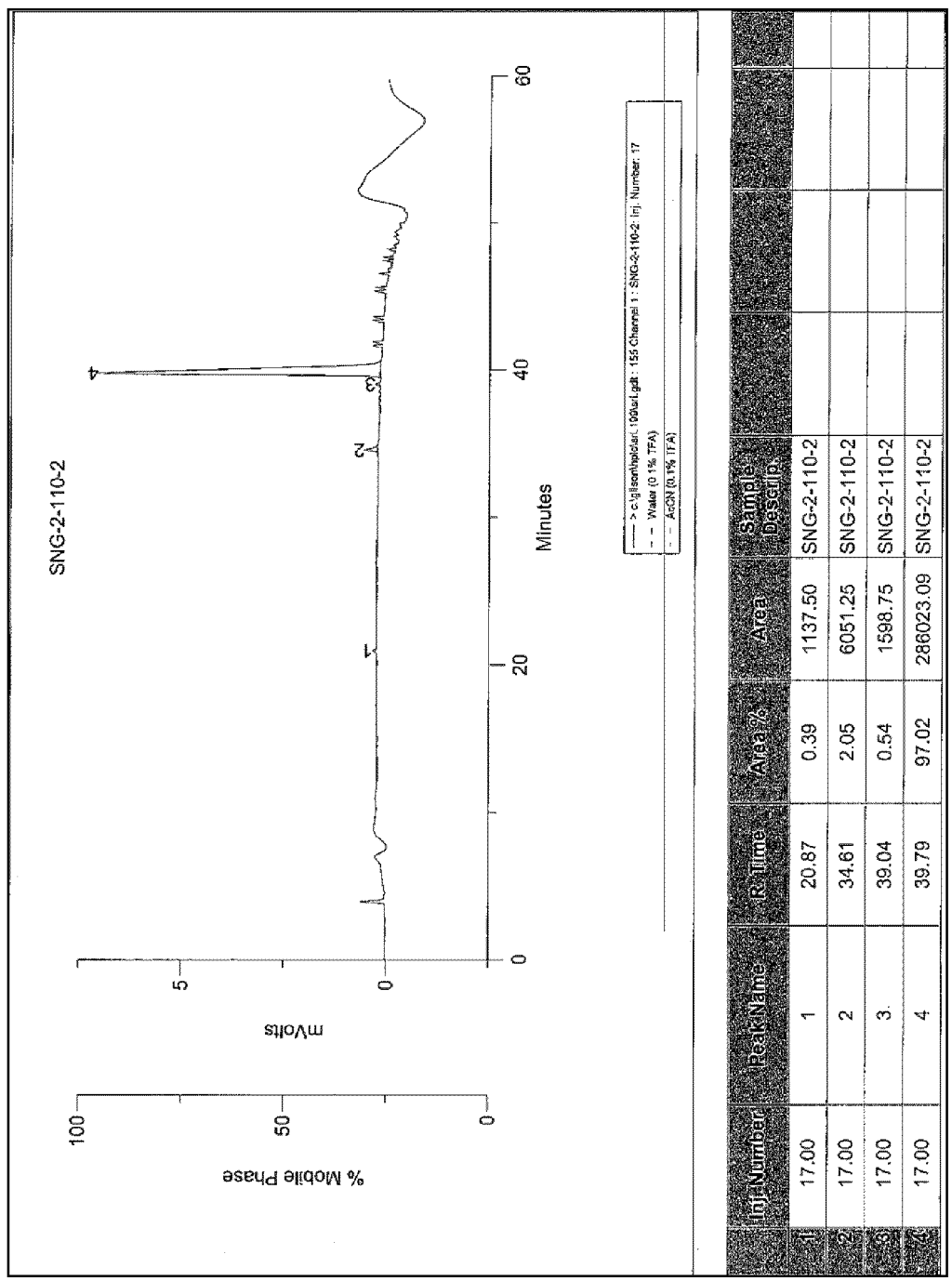
FIG. 6A is a graph that shows the HPLC profile for an exemplary compound GP003-9 (SEQ ID NO: 6).
Figure 6B:
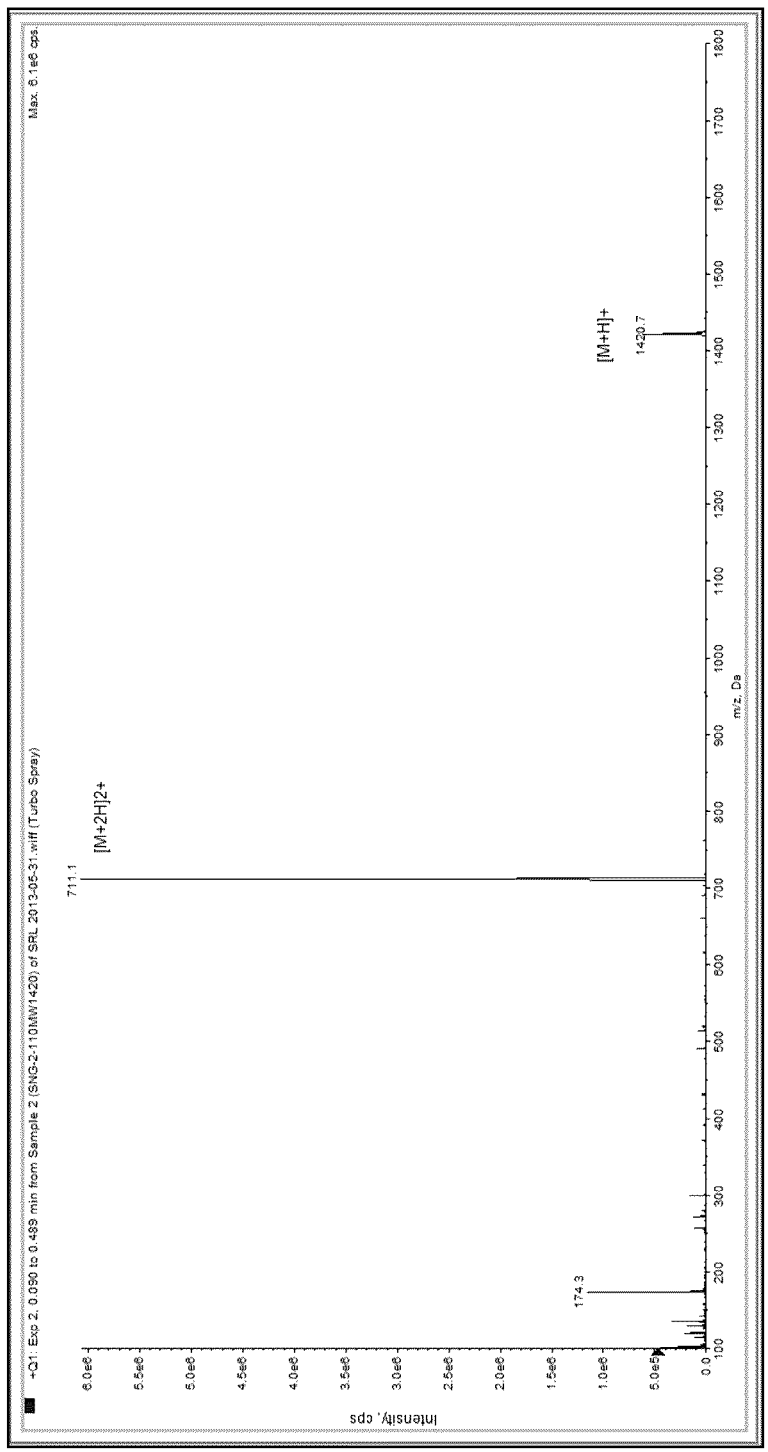
FIG. 6B is a graph that shows the Mass Spectrometry for an exemplary compound GP003-9 (SEQ ID NO: 6).

GP003-9 (Pal-KT(Ac$_7$-β-Mal)TKS-OH) (SEQ ID NO: 6)—Material: Glycopeptide (β-Maltose peptide PerAc); Molecular weight: 1420; Appearance: white lyophilized solid; Purity (HPLC) >97% (FIG. 6A); Mass Spectrometry (ESI POS): conforms [M+H]=1420.7 (FIG. 6B).

Figure 7A:
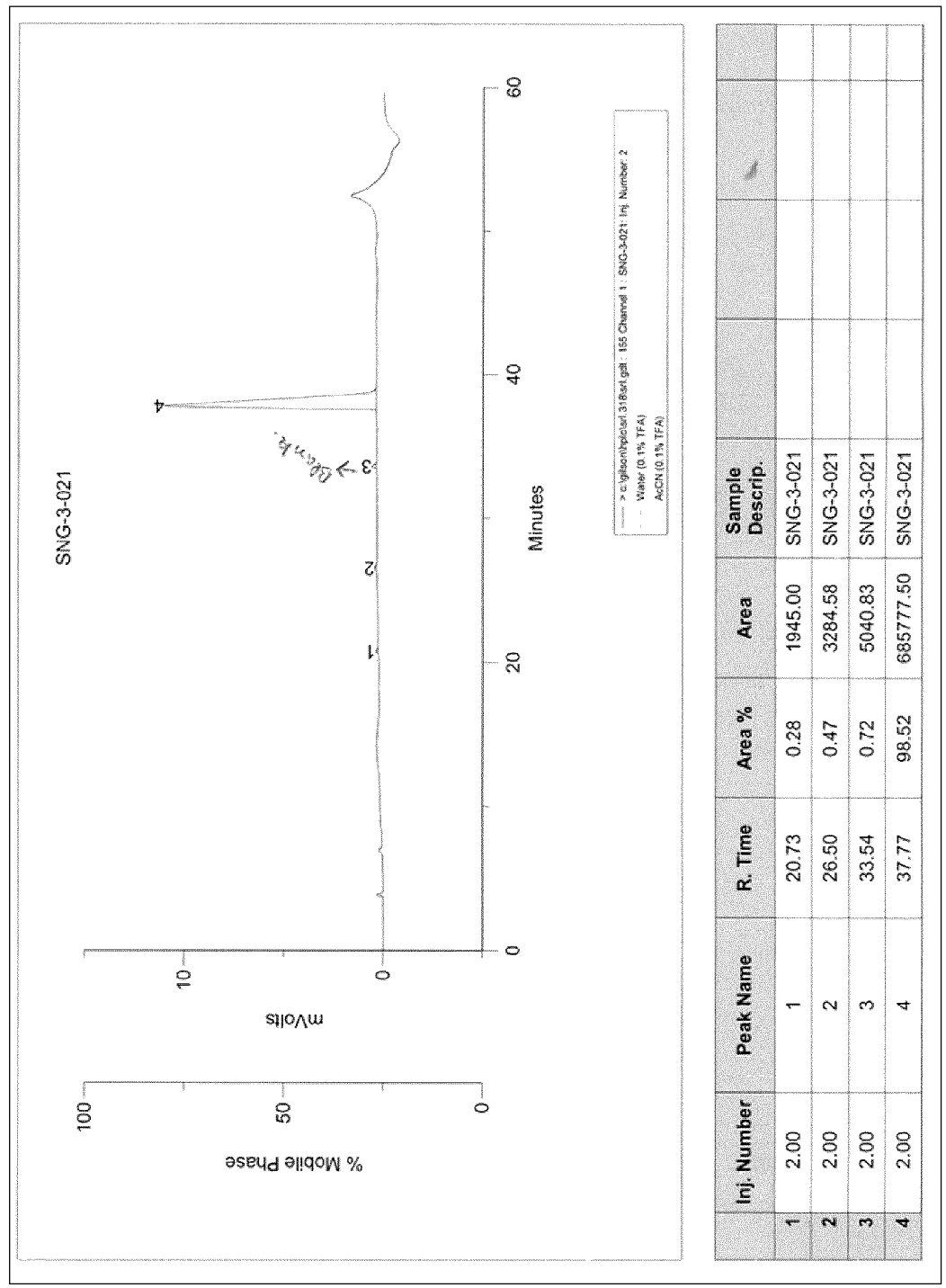
FIG. 7A is a graph that shows the HPLC profile for an exemplary compound GP004-3 (SEQ ID NO: 9).
Figure 7B:
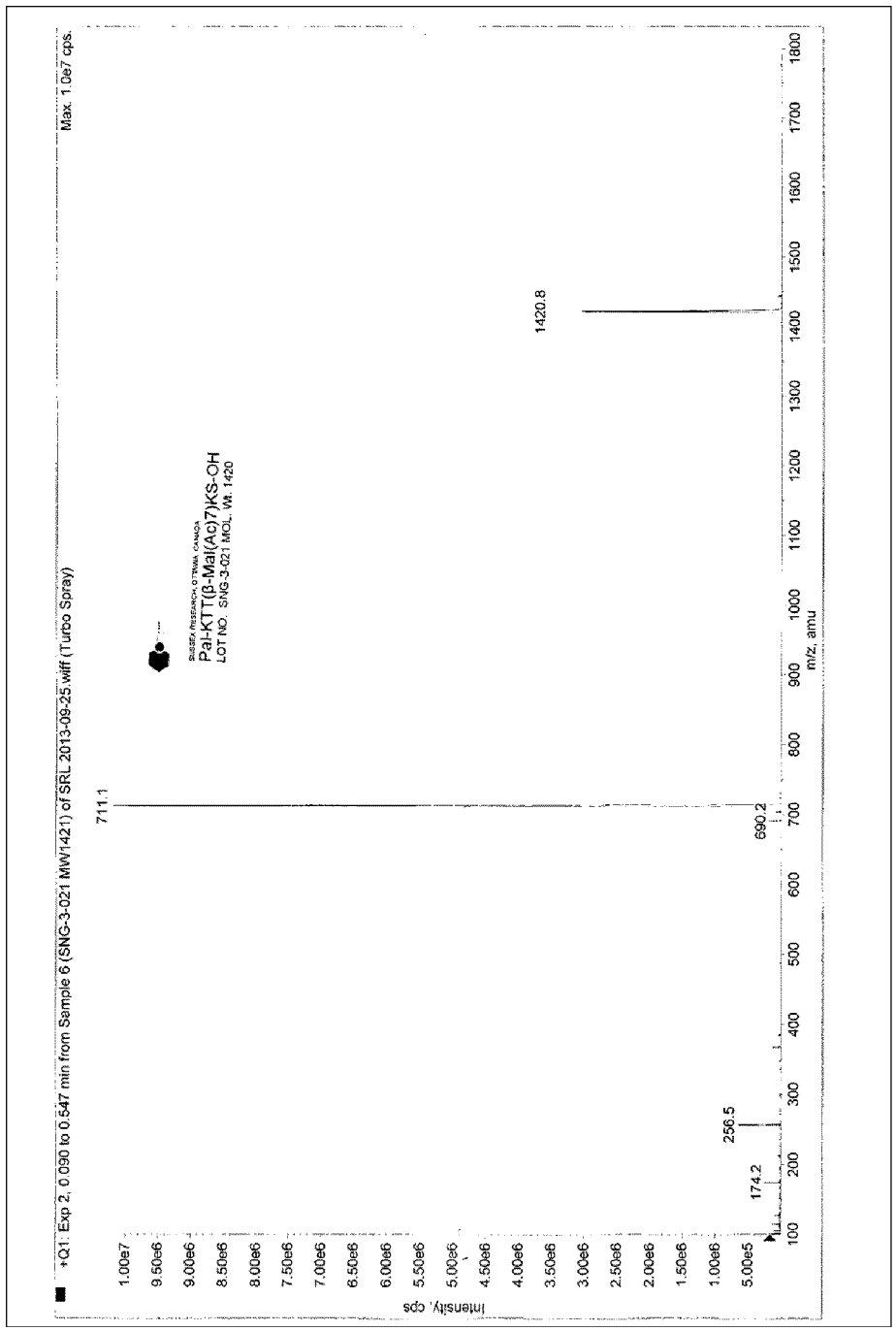
FIG. 7B is a graph that shows the Mass Spectrometry for an exemplary compound GP004-3 (SEQ ID NO: 9).

GP004-3 (Pal-KTT(Ac$_7$-β-Mal)KS-OH) (SEQ ID NO: 9)—Material: Glycopeptide (β-Maltose peptide PerAc);

Molecular weight: 1420; Appearance: white lyophilized solid; Purity (HPLC) >95% (FIG. 7A); Mass Spectrometry (ESI POS): conforms [M+H]=1420.8 (FIG. 7B).

Figure 8A:
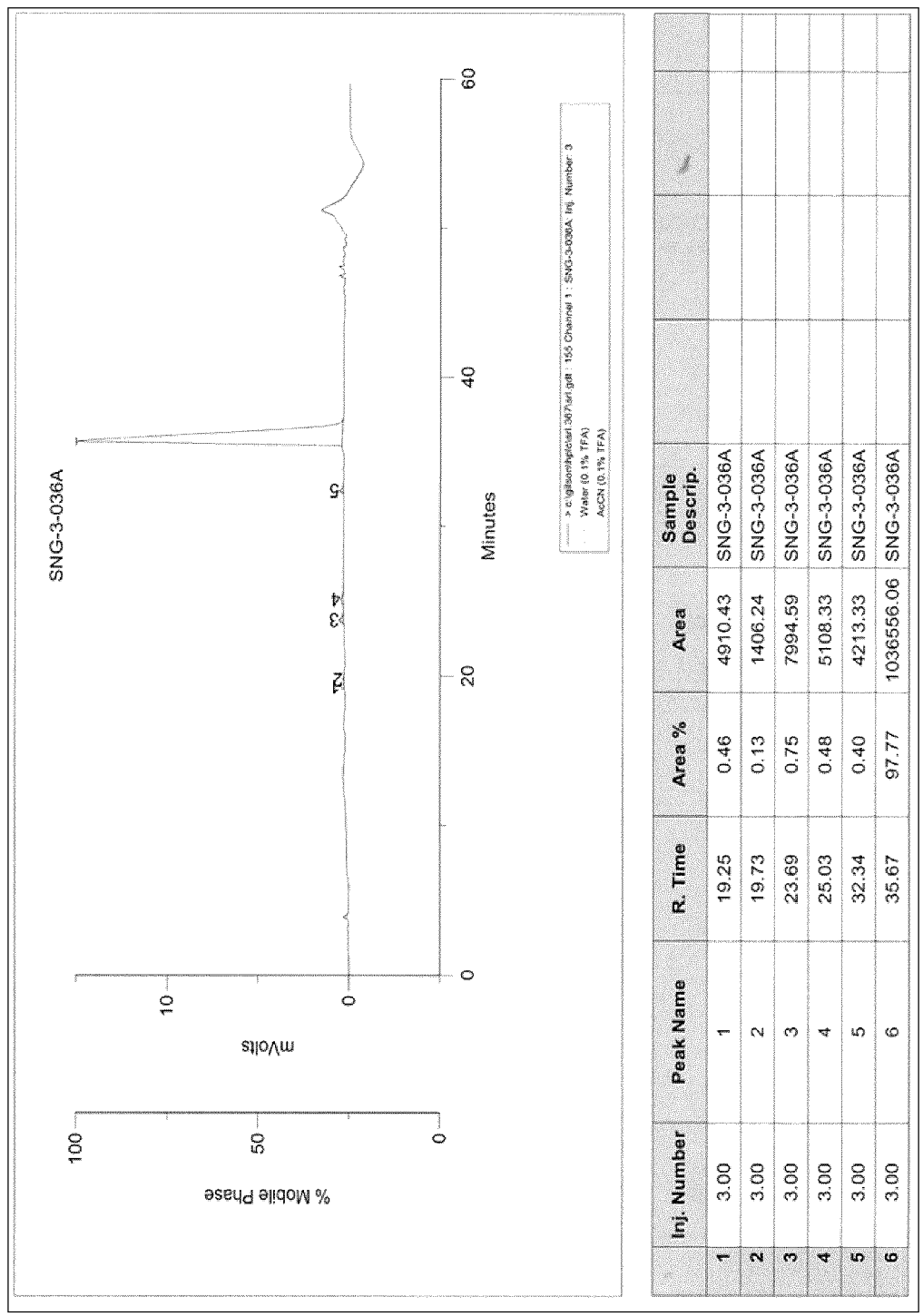
FIG. 8A is a graph that shows the HPLC profile for an exemplary compound GP004-4 (SEQ ID NO: 10).
Figure 8B:
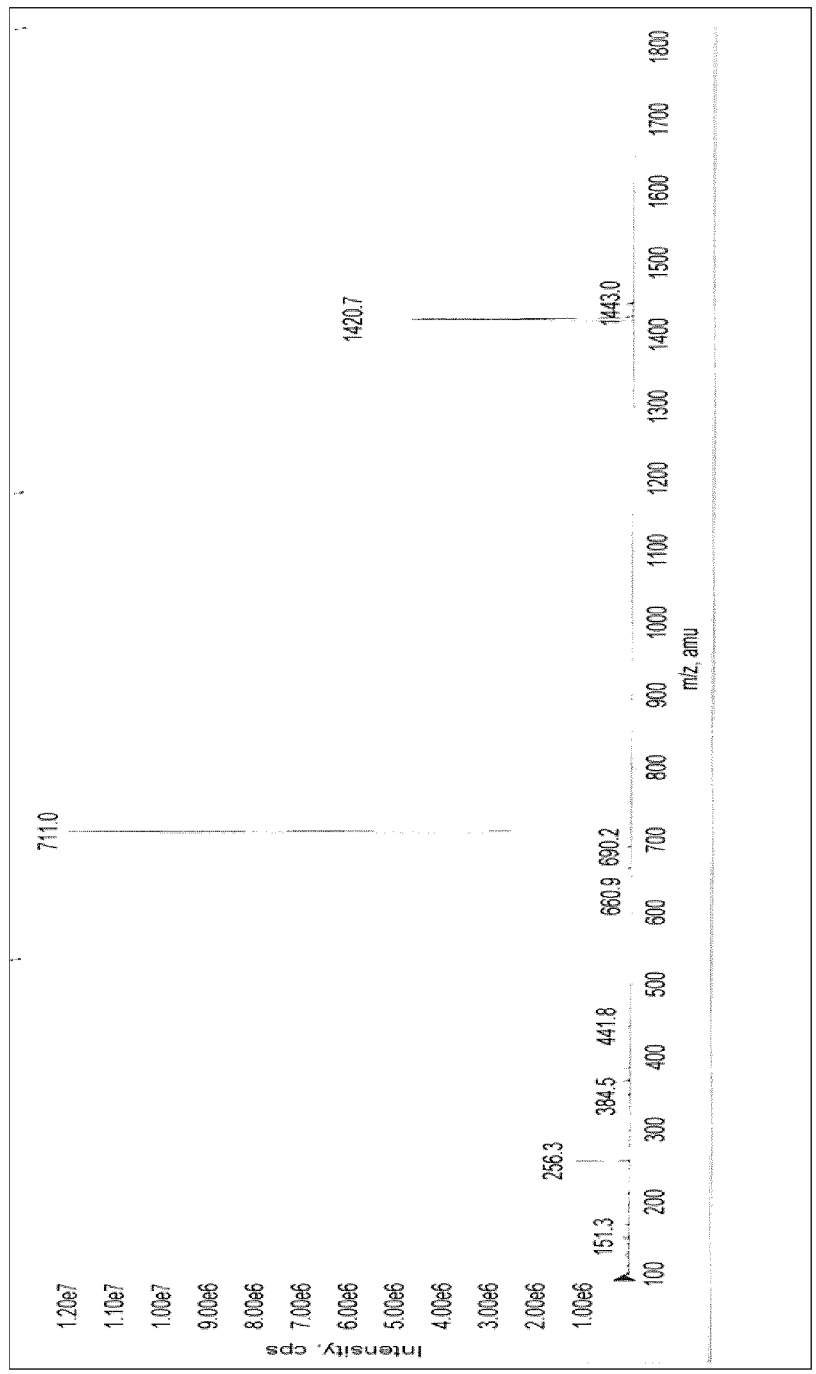
FIG. 8B is a graph that shows the Mass Spectrometry for an exemplary compound GP004-4 (SEQ ID NO: 10).

GP004-4 (Pal-KTTKS(Ac$_7$-β-Mal)-OH) (SEQ ID NO: 10)—Material: Glycopeptide (β-Maltose peptide PerAc); Molecular weight: 1420; Appearance: white lyophilized solid; Purity (HPLC) >95% (FIG. 8A); Mass Spectrometry (ESI POS): conforms [M+H]=1420.7 (FIG. 8B).

These 6 glycosylated pentapeptides were subjected to in vitro toxicity testing (cell viability and morphology) in comparison to the reference pentapeptide Pal-KKTKS (SEQ ID NO: 2).

Figure 9:
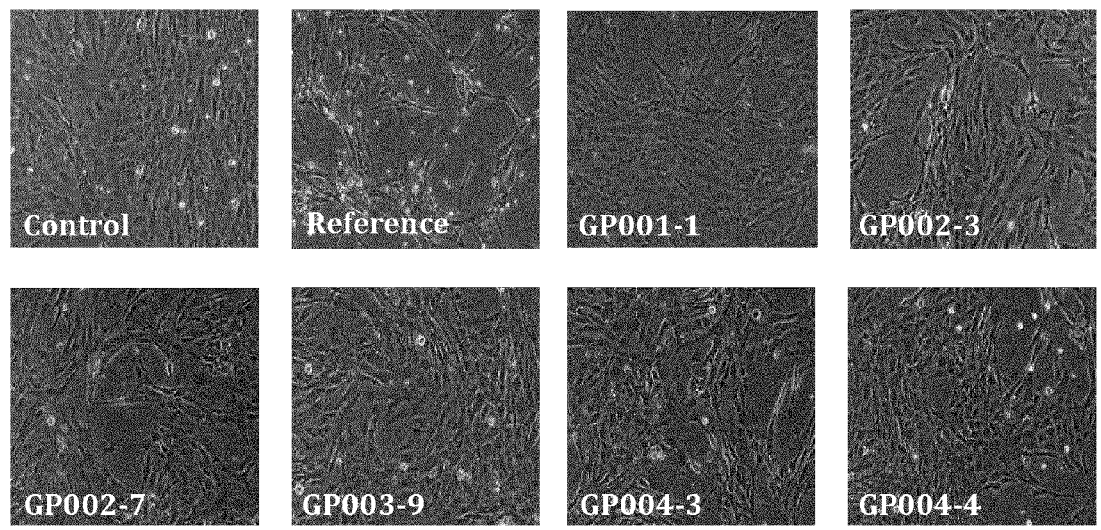
FIG. 9 shows phase contrast images showing the effect of six exemplary glycopeptides (GP001-1, GP002-3, GP002-7, GP003-9, GP004-3 and GP004-4 (SEQ ID Nos: 4, 8, 7, 6, 9 and 10, respectively)), as well as the unglycosylated Pal-KTTKS reference peptide (SEQ ID NO: 2), on cell morphology.

To determine effects on cell morphology and size, 5 μM of the 6 exemplary glycopeptides were applied to Human Dermal Fibroblasts (KMST-6) as previously described. The reference pentapeptide was Pal-KTTKS (SEQ ID NO: 2) (CPC Scientific, 822197), and control sample cells were treated with DMSO (Fisher, BP231-100). Morphological images showed that the reference visibly interfered with cell viability and there was a demonstrated decrease in cell confluence compared to control and glycopeptide treated cells. While in contrast none of the 6 glycopeptides tested showed any form of toxicity as observed through phase-contrast morphology (FIG. 9). Importantly 90% of all glycopeptides tested at 5 μM concentration did not show any form of toxicity as measured by MTT-assay (data not shown).

Figure 10A:
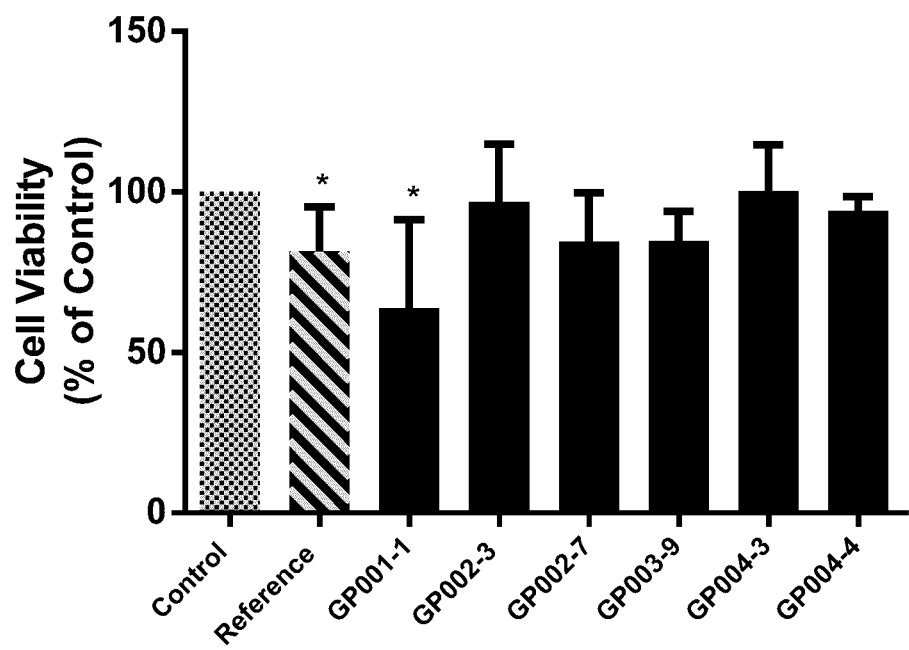
FIG. 10A is a graph showing the comparison of the effect of six exemplary glycopeptides (GP001-1, GP002-3, GP002-7, GP003-9, GP004-3 and GP004-4 (SEQ ID Nos: 4, 8, 7, 6, 9 and 10, respectively)), as well as the unglycosylated Pal-KTTKS reference peptide (SEQ ID NO: 2), on cell viability after 48 hours (as measured by MTT assay).
Figure 10B:
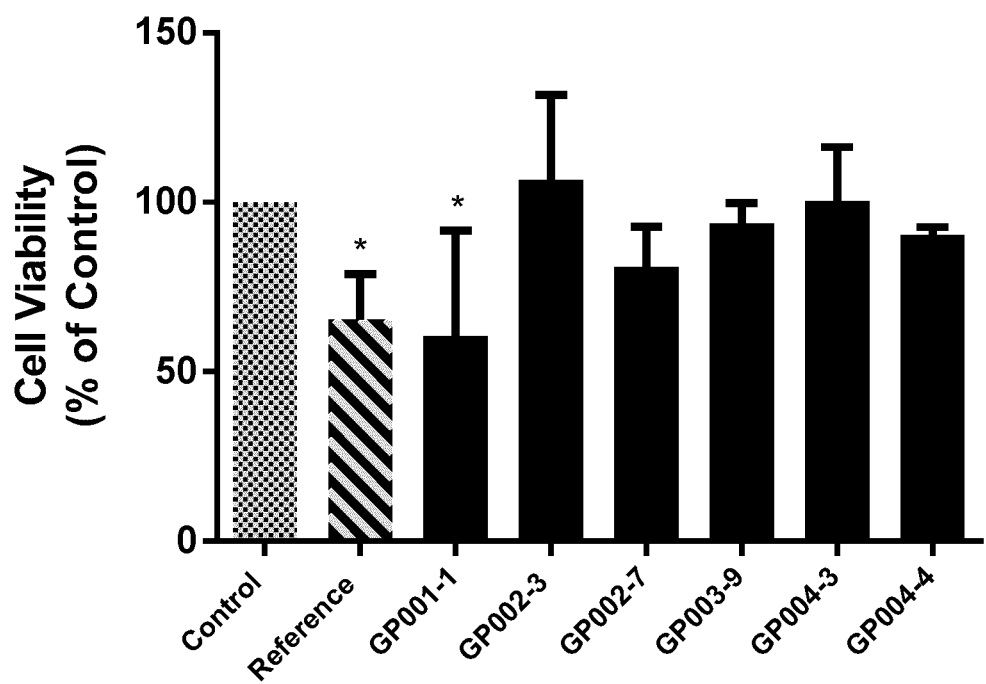
FIG. 10B is a graph showing the comparison of the effect of six exemplary glycopeptides (GP001-1, GP002-3, GP002-7, GP003-9, GP004-3 and GP004-4 (SEQ ID Nos: 4, 8, 7, 6, 9 and 10, respectively)), as well as the unglycosylated Pal-KTTKS reference peptide (SEQ ID NO: 2), on cell viability after 72 hours (as measured by MTT assay).

To determine effects on cell viability as a measure of toxicity, 5 μM of the 6 exemplary glycopeptides were applied to Human Dermal Fibroblasts (KMST-6) as previously described. The reference pentapeptide was Pal-KTTKS (SEQ ID NO: 2) (CPC Scientific, 822197), and control sample cells were treated with DMSO (Fisher, BP231-100). As described previously treated cells were incubated at 37° C. and 5% CO$_2$ for 48 hours (FIG. 10A) and 72 hours (FIG. 10B). At each timepoint, the MTT Assay was performed by adding 15 μL of the Dye Solution (Promega, G4102) to all wells. Cells were incubated for 2-4 hours during which time viable cells convert the MTT tetrazolium component of the Dye Solution into a formazan product. Solubilization/Stop Solution (Promega, G4101) was then added to the culture wells to solubilize the formazan product. The absorbance was measured with a microplate reader (Molecular Devices, SpectraMax M2e) at 570 nm. Three or more independent experiments were performed and statistical significance was determined using One-way ANOVA (p<0.05). Toxicity was defined as the cell viability that is less than 50% when compared to control. Only one of the 6 glycopeptides tested showed an effect on cell viability at either time point (FIGS. 10A and 10B). In contrast, the unglycosylated reference pentapeptide showed a significant decrease in cell viability at 48 and 72 hours (FIG. 10B) compared to control. Importantly 90% of all glycopeptides tested at 5 μM concentration did not show any form of toxicity as measured by MTT-assay (data not shown).

To further characterize and investigate the toxicity profile of the glycopeptides, additional experiments were performed testing glycopeptides GP003-9, GP004-3 and GP004-4 (SEQ ID Nos: 6, 9 and 10, respectively) (data not shown). Human dermal fibroblasts (KMST-6) were treated with 5 μM glycopeptides, reference (Pal-KTTKS (SEQ ID NO: 2), CPC Scientific, 822197) and control (DMSO, Fisher, BP231-100) at 48 and 72 hours. The following toxicity assays were conducted: 1) Cell viability (CellTiter 96® AQueous One Solution (MTS) colourimetric assay, Promega, G3580) for the measurement of cell metabolic activity; 2) LIVE/DEAD® Viability/Cytotoxicity Kit (Molecular Probes, L-3224) for measurement of the live cells per total cell population; 3) Cell proliferation by measuring: a) cell counts to obtain total live cell number and b) DNA content (PureLink® Genomic DNA Mini Kit, Invitrogen, K182002) for quantifying cells with intact DNA and lastly; 4) Apoptosis/Necrosis (Dead Cell Apoptosis Kit with Annexin V Alexa Fluor® 488 & Propidium Iodide, Molecular Probes, V13241) for measurement of cells undergoing cell death. In all the additional experiments performed, there was no toxicity observed with the three glycopeptides subjected to additional in vitro toxicity testing.

To confirm effects on extracellular matrix protein secretion, Human dermal fibroblasts (KMST-6) were treated with 5 μM glycopeptides [GP001-1 (Pal-KT(Ac$_4$-Glc)TKS-OH), GP002-3 ((Pal-KTTKS(Ac$_4$-Glc)-OH), GP002-7 (Pal-KTTKS(Ac$_4$-Gal)-OH), GP003-9 (Pal-KT(Ac$_7$-β-Mal)TKS-OH), GP004-3 (Pal-KTT(Ac$_7$-β-Mal)KS-OH) and GP004-4 (Pal-KTTKS(Ac$_7$-β-Mal)-OH) (SEQ ID Nos: 4, 8, 7, 6, 9 and 10, respectively)], reference (Pal-KTTKS (SEQ ID NO: 2), CPC Scientific, 822197) or vehicle control (DMSO, Fisher, BP231-100) for 72 hours. Three or more independent experiments were performed. Statistical significance was performed using One-way ANOVA (p<0.05) where '*' represents statistical significance when compared to control and "#" represents statistical significance when compared to reference.

TABLE 6

ECM Protein Summary Table

| Compound # | ELASTIN | FIBRONECTIN | TOTAL COLLAGEN |
|---|---|---|---|
| Control | 100% | 100% | 100% |
| Reference | 133 | 118 | 110 |
| GP001-1 | 188 | 122 | |
| GP002-3 | 322*# | 135* | |
| GP002-7 | 207* | 116 | |
| GP003-9 | 284*# | 140* | 125* |
| GP004-3 | 385*# | 168*# | 131*# |
| GP004-4 | 186 | 183*# | 124* |

Figure 11A:
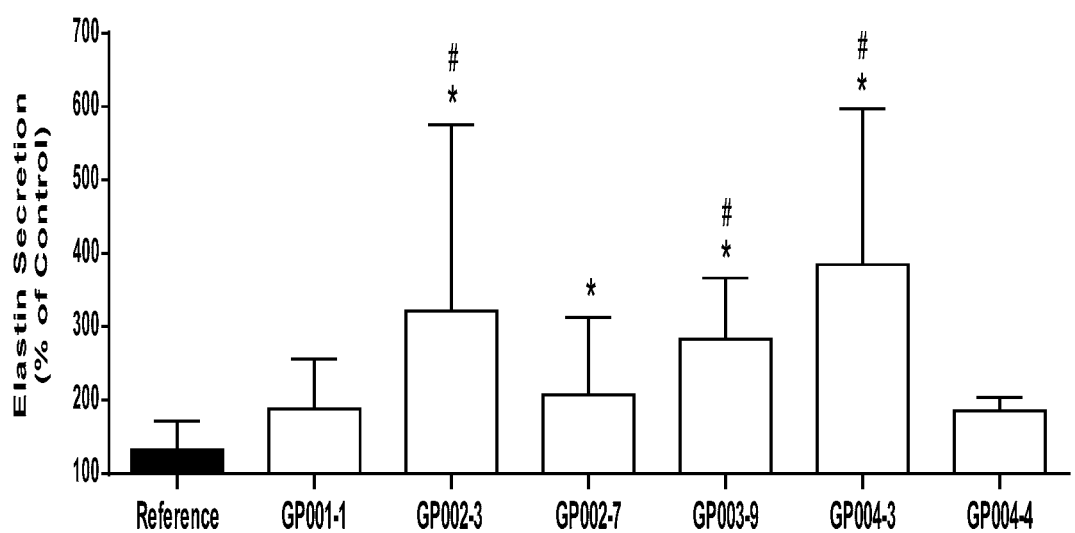
FIG. 11A is a graph showing the comparison of the efficacy of six exemplary glycopeptides (GP001-1, GP002-3, GP002-7, GP003-9, GP004-3 and GP004-4 (SEQ ID Nos: 4, 8, 7, 6, 9 and 10, respectively)), as well as the unglycosylated Pal-KTTKS reference peptide (SEQ ID NO: 2), on elastin secretion as % of control at 72 hours post-treatment of human dermal fibroblasts.
Figure 11B:
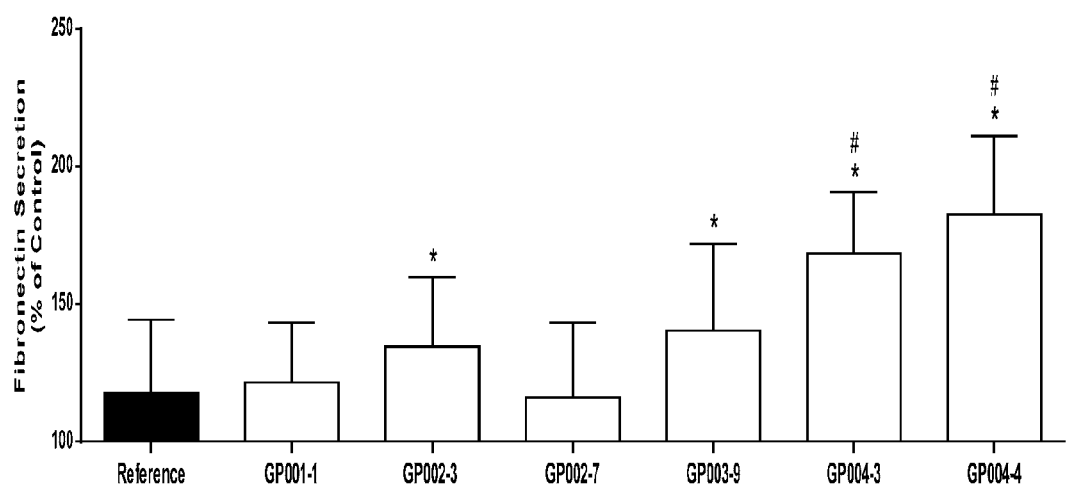
FIG. 11B is a graph showing the comparison of the efficacy of six exemplary glycopeptides (GP001-1, GP002-3, GP002-7, GP003-9, GP004-3 and GP004-4 (SEQ ID Nos: 4, 8, 7, 6, 9 and 10, respectively)), as well as the unglycosylated Pal-KTTKS reference peptide (SEQ ID NO: 2), on fibronectin secretion as % of control at 72 hours post-treatment of human dermal fibroblasts.

GP001-1, GP002-3, GP002-7, GP003-9, GP004-3 and GP004-4 (SEQ ID Nos: 4, 8, 7, 6, 9 and 10, respectively) all induced greater biological activity in elastin (Table 6 and FIG. 11A) and fibronectin (Table 6 and FIG. 11B) secretion compared to control. However, glycopeptides GP002-3 (189%, p<0.0001), GP003-9 (151%, p<0.0001) and GP004-3 (252%, p<0.0001) (SEQ ID Nos: 8, 6 and 9, respectively) significantly increased secretion of elastin compared to the reference peptide while GP002-3 (222%, p<0.0001), GP002-7 (107%, p<0.04), GP003-9 (184%, p<0.0001) and GP004-3 (285%, p<0.0001) (SEQ ID Nos: 8, 7, 6, and 9, respectively) significantly increased elastin secretion compared to control. Additionally, GP004-3 (50%, p<0.02) and GP004-4 (65%, p<0.0007) (SEQ ID Nos: 9 and 10, respectively) significantly increased fibronectin secretion compared to reference whereas GP002-3 (35%, p<0.01), GP003-9 (40%, p<0.0004)), GP004-3 (68%, p<0.0003) and GP004-4 (83%, p<0.0001) (SEQ ID Nos: 8, 6, 9 and 10, respectively) significantly increased fibronectin secretion compared to control. Lastly, GP003-9, GP004-3 and GP004-4 (SEQ ID Nos: 6, 9 and 10, respectively) were the only glycopeptides tested for total collagen and results showed that they all significantly increased total collagen secretion by 25% (p<0.004), 31% (p<0.0008) and 24% (p<0.005) compared to control, respectively, and GP004-3

Figure 12:
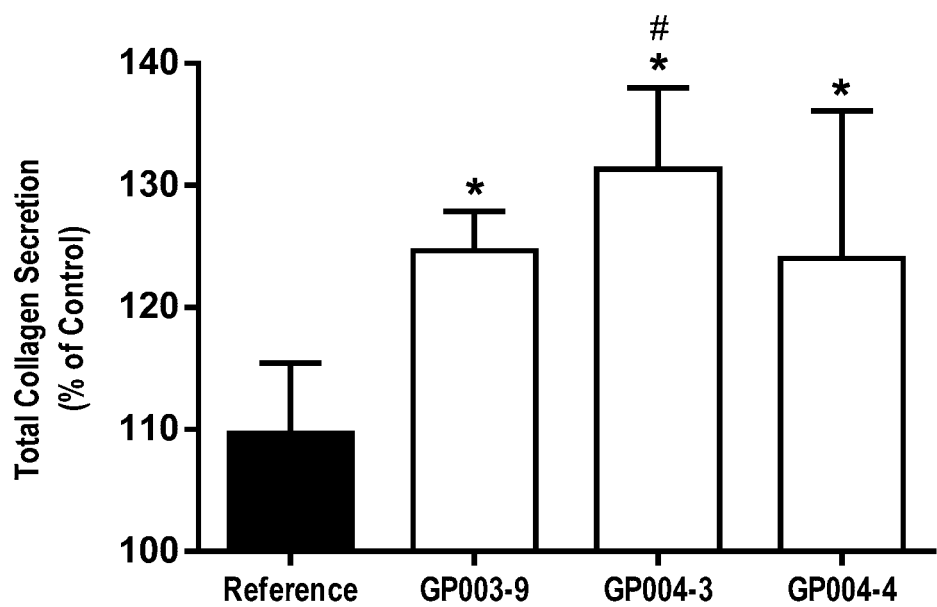
FIG. 12 is a graph showing the comparison of the efficacy of three exemplary glycopeptides (GP003-9, GP004-3 and GP004-4 (SEQ ID Nos: 6, 9 and 10, respectively)), as well as the unglycosylated Pal-KTTKS reference peptide (SEQ ID NO: 2), on total collagen secretion as % of control at 72 hours post-treatment of human dermal fibroblasts.

(21%, p<0.01) (SEQ ID NO: 9) significantly increased total collagen secretion compared to the reference peptide (Table 6 and FIG. 12).

Figure 13:
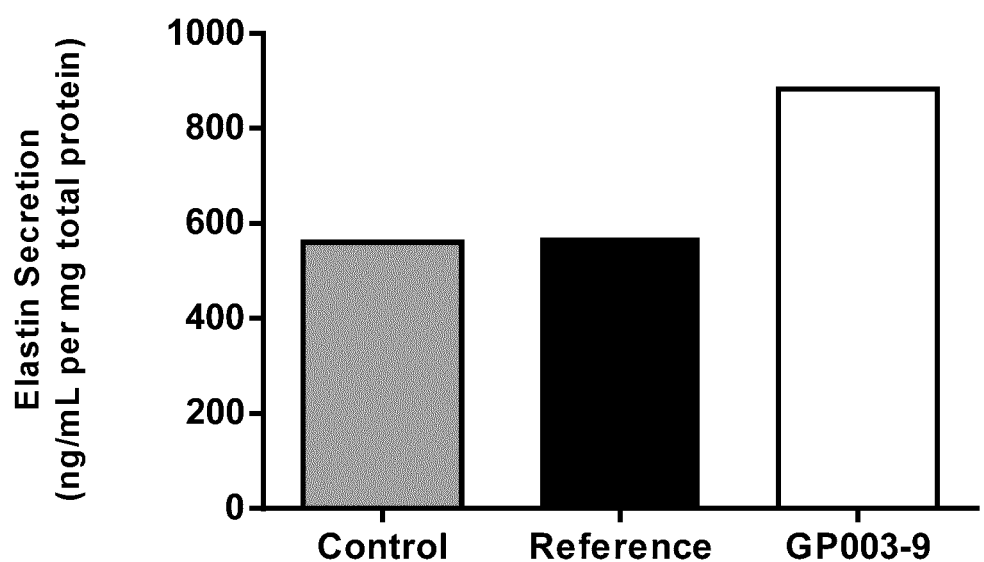
FIG. 13 is a graph showing the efficacy of an exemplary glycopeptide GP003-9 (SEQ ID NO: 6), as well as the unglycosylated Pal-KTTKS reference peptide (SEQ ID NO: 2), on elastin secretion as % of control at 72 hours post-treatment in an in vitro 3D model of human skin (comprised of human epidermal keratinocytes and human dermal fibroblasts).
Figure 14:
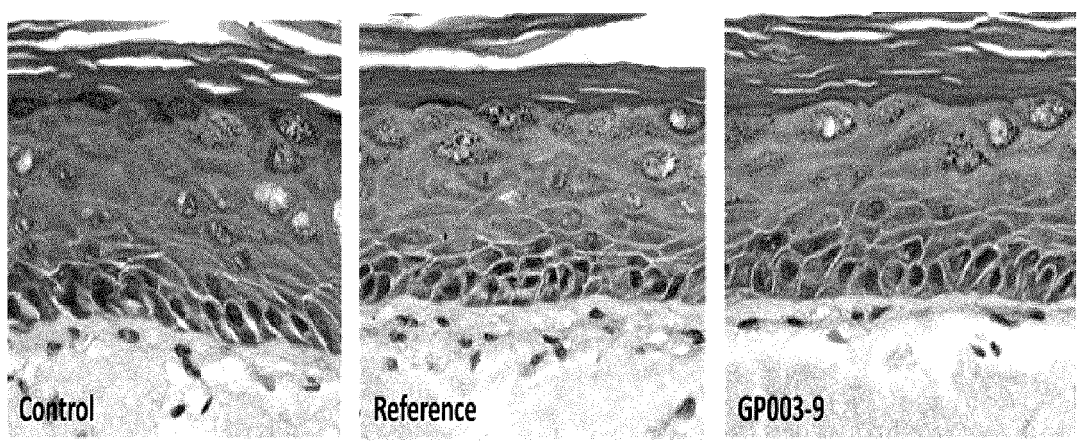
FIG. 14 shows photomicrographs of Hematoxylin & Eosin stained sections of an in vitro 3-D model of human skin (comprised of human epidermal keratinocytes and human dermal fibroblasts) showing the effect on morphology of an exemplary glycopeptide GP003-9 (SEQ ID NO: 6), as well as the unglycosylated Pal-KTTKS reference peptide (SEQ ID NO: 2).

MatTek's EpiDermFT™, which is a 3D human in vitro skin model (comprised of normal human epidermal keratinocytes and normal human dermal fibroblasts), was used to further investigate the effects of an exemplary glycosylated peptide (GP003-9 (SEQ ID NO: 6)) on human skin. Tissues were treated with 5 μM GP003-9 (SEQ ID NO: 6), reference (Pal-KTTKS (SEQ ID NO: 2), CPC Scientific, 822197), or vehicle control (DMSO, Fisher, BP231-100) as previously described. At 72 hours post treatment, supernatants were isolated and analysed for elastin secretion. FIG. 13 shows that GP003-9 (SEQ ID NO: 6) increased elastin secretion in a 3D human skin model approximately 1.5 fold in comparison to unglycosylated reference peptide or control. Alternatively tissues treated with 5 μM GP003-9 (SEQ ID NO: 6), reference (Pal-KTTKS (SEQ ID NO: 2), CPC Scientific, 822197), or vehicle control (DMSO, Fisher, BP231-100) were paraffin embedded, sectioned and then stained with hematoxylin & eosin for histological assessment. FIG. 14 shows that GP003-9 (SEQ ID NO: 6) had no detrimental effect on the histology of the 3D human skin model.

The above-described examples are intended to be exemplary only. Alterations, modifications and variations can be effected to the particular examples by those of skill in the art without departing from the scope, which is defined solely by the claims appended hereto.

What is claimed is:

1. A 5 or 6 amino acid glycosylated oligopeptide of the formula:

Palmitoyl-X1-Lys-X2-X3-Lys-X4-OH (SEQ ID NO: 3), wherein:
X1 is: absent, Ser having a glycosylated side chain, or Asn having a glycosylated side chain;
X2 is: Thr, Thr having a glycosylated side chain, Asn having a glycosylated side chain, or Ser having a glycosylated side chain;
X3 is: Thr, or Thr having a glycosylated side chain;
X4 is: Ser, or Ser having a glycosylated side chain;
wherein: at least one of X1, X2, X3 and X4 is an amino acid having a glycosylated side chain;
wherein: each glycosylated side chain is, independently, glycosylated with a carbohydrate selected from the group consisting of: glucose, N-acetyl-glucosamine, galactose, N-acetyl-galactosamine, mannose, maltose, lactose, rhamnose, cellobiose, xylose, and fucose; and
wherein: each hydroxyl group on the carbohydrate is, independently, OH or acetylated.

2. The glycosylated oligopeptide according to claim 1, wherein the hydroxyl groups on the carbohydrate are all acetylated.

3. The glycosylated oligopeptide according to claim 1, wherein the hydroxyl groups on the carbohydrate are all not acetylated.

4. The glycosylated oligopeptide according to claim 1, wherein X1 is absent.

5. The glycosylated oligopeptide according to any one of claims 1-4, wherein X2 is Thr having a glycosylated side chain.

6. The glycosylated oligopeptide according to claim 5, wherein the glycosylated side chain is glycosylated with glucose, mannose or maltose.

7. The glycosylated oligopeptide according to claim 5, wherein X1, X3 and X4 amino acids are unglycosylated.

8. The glycosylated oligopeptide according to any one of claims 1-4, wherein X4 is Ser having a glycosylated side chain.

9. The glycosylated oligopeptide according to claim 8, wherein the glycosylated side chain is glycosylated with glucose, galactose or maltose.

10. The glycosylated oligopeptide according to claim 8, wherein X1, X2 and X3 amino acids are unglycosylated.

11. The glycosylated oligopeptide according to any one of claims 1-4, wherein X3 is Thr having a glycosylated side chain.

12. The glycosylated oligopeptide according to claim 11, wherein X1, X2 and X4 amino acids are unglycosylated.

13. A glycosylated oligopeptide consisting of the amino acid sequence: Palmitoyl-Lys-Thr*-Thr-Lys-Ser-OH, wherein Thr* is threonine glycosylated with per-acetylated β-glucose (SEQ ID NO: 4).

14. A glycosylated oligopeptide consisting of the amino acid sequence: Palmitoyl-Lys-Thr*-Thr-Lys-Ser-OH, wherein Thr* is threonine glycosylated with per-acetylated α-mannose (SEQ ID NO: 5).

15. A glycosylated oligopeptide consisting of the amino acid sequence: Palmitoyl-Lys-Thr*-Thr-Lys-Ser-OH, wherein Thr* is threonine glycosylated with per-acetylated β-maltose (SEQ ID NO: 6).

16. A glycosylated oligopeptide consisting of the amino acid sequence: Palmitoyl-Lys-Thr-Thr-Lys-Ser*-OH, wherein Ser* is serine glycosylated with per-acetylated β-galactose (SEQ ID NO: 7).

17. A glycosylated oligopeptide consisting of the amino acid sequence: Palmitoyl-Lys-Thr-Thr-Lys-Ser*-OH, wherein Ser* is serine glycosylated with per-acetylated β-glucose (SEQ ID NO: 8).

18. A glycosylated oligopeptide consisting of the amino acid sequence: Palmitoyl-Lys-Thr-Thr*-Lys-Ser-OH, wherein Thr* is threonine glycosylated with per-acetylated β-maltose (SEQ ID NO: 9).

19. A glycosylated oligopeptide consisting of the amino acid sequence: Palmitoyl-Lys-Thr-Thr-Lys-Ser*-OH, wherein Ser* is serine glycosylated with per-acetylated β-maltose (SEQ ID NO: 10).

20. A glycosylated oligopeptide consisting of the amino acid sequence according to any one of SEQ ID NOs: 12-48.

21. A cosmetic or dermopharmaceutical composition comprising at least one glycosylated oligopeptide according to any one of claims 1-4, and 13-20.

22. A method of increasing the secretion of an extra-cellular matrix protein by a cell in an individual in need thereof, the method comprising topically administering to the individual the composition according to claim 21.

23. The method according to claim 22, wherein the extra-cellular matrix protein is elastin, fibronectin, or collagen.

24. A skin care composition comprising:
a) a safe and effective amount of a glycosylated oligopeptide according to any one of claims 1-4, and 13-20;
b) a safe and effective amount of at least one additional skin care agent selected from the group consisting of: desquamatory agents, anti-acne agents, vitamin A compounds, vitamin $B_3$ compounds, vitamin C compounds, vitamin E compounds, carotenoids, retinoids, di-, tri-, tetra-, penta- and hexa-peptides and derivatives thereof, hydroxy acids, radical scavengers, chelators, anti-inflammatory agents, topical anesthetics, tanning agents, skin lightening agents, sunscreen agents, anti-cellulite agents, flavonoids, antimicrobial agents, skin healing agents, farnesol, phytantriol, allantoin, glucosamine, hyaluronic acids and mixtures thereof; and
c) a dermatologically acceptable carrier.

25. The skin care composition according to claim 24, wherein the antimicrobial agent is an antifungal agent.

* * * * *